United States Patent
Osanai et al.

(10) Patent No.: US 7,049,079 B1
(45) Date of Patent: May 23, 2006

(54) COUPLING FACTOR 6 INHIBITOR AND POTENTIATOR AND USE THEREOF

(75) Inventors: Tomohiro Osanai, Nakatsugaru-gun (JP); Koji Magota, Takatsuki (JP)

(73) Assignee: Daiichi Suntory Pharma Co.,Ltd., Tokyo (JP)

( * ) Notice: Subject to any disclaimer, the term of this patent is extended or adjusted under 35 U.S.C. 154(b) by 544 days.

(21) Appl. No.: 09/831,951

(22) PCT Filed: Aug. 3, 2000

(86) PCT No.: PCT/JP00/05210

§ 371 (c)(1),
(2), (4) Date: Aug. 14, 2001

(87) PCT Pub. No.: WO01/21205

PCT Pub. Date: Mar. 29, 2001

(30) Foreign Application Priority Data

Sep. 17, 1999  (JP) ................................ 11/264687

(51) Int. Cl.
*G01N 33/53* (2006.01)
(52) U.S. Cl. ....................................... 435/7.1; 436/501
(58) Field of Classification Search ................ 435/7.1; 436/501
See application file for complete search history.

(56) References Cited

U.S. PATENT DOCUMENTS

| 5,663,315 A | * | 9/1997 | Scheele et al. ............ 536/23.5 |
| 5,849,527 A |   | 12/1998 | Hillman et al. |
| 6,048,718 A |   | 4/2000 | Hillman et al. |

OTHER PUBLICATIONS

Osani, T. et al. "Coupling factor is a novel endogenous inhibitory peptide . . . in endothelial Cells" CIRCULATION, vol. 98, No. 17, p. 1529, Oct. 27, 1998, XP009031815 Abstract.

Osanai et al., A novel inhibitory effect on prostacyclin synthesis of coupling factor 6 extracted from the heart of spontaneously hypertensive rats,J. Biol Chem, 1998, pp. 31778-31783.

Ando et al, Differential display and cloning of shear stress-responsive messenger RNAs in human endothelial cells, Biochem & Biophy Res Comm. 1996, pp. 347-351.

Evans et al, An import-competant precursor of small subunit of ribulose-1,5-bisphosphate carboxylase generated by factor Xa cleavage from a beta-glactosidase fusion expressed in *Escherichia coli*, Protein Expr Purif, 1992, pp. 178-184.

* cited by examiner

*Primary Examiner*—Patrick J. Nolan
(74) *Attorney, Agent, or Firm*—Paul E. White, Jr.; Manelli Denison & Selter PLLC

(57) ABSTRACT

Methods of measuring the presence/absence of a coupling factor 6, which is a subunit of $H^+$-transporting ATP synthase→$H^+$ ATP synthase present in the mitochondrial inner membrane, in the blood and the concentration thereof are provided. Further, relations among the coupling factor 6 level in the blood and diseases and relations among the inhibition of the effect of the coupling factor and therapeutic effects on diseases are clarified and thus techniques for diagnosing and treating these diseases are provided.

The present invention provides a vector containing a DNA encoding the coupling factor 6 or fragment thereof; a transformant transformed by this vector; and a method of producing the coupling factor 6 and its fragment. The present invention further provides an antibody reacting specifically with the coupling factor 6; a process of producing the antibody; and a method of assaying the coupling factor 6.

11 Claims, 25 Drawing Sheets

** : $p < 0.02$
* : $p < 0.05$

** : p < 0.02
* : p < 0.05

* : p < 0.05

* : p < 0.01

*p<0.05 vs. the level before administration
**p<0.01 vs. the level before administration

# COUPLING FACTOR 6 INHIBITOR AND POTENTIATOR AND USE THEREOF

TECHNICAL FIELD

This invention relates to diagnostic methods and a diagnostic aid for judging the onset and progress of diseases associated with a change in the coupling factor (CF6) level in the blood, diseases in association with the excess or shortage of $PGI_2$ or diseases associated with the accentuation or attenuation of $cPLA_2$ function, which may be referred to as $cPLA_2$ hyperfunction or $cPLA_2$ hypofunction and a pharmaceutical composition for the treatment of these diseases. The present invention further relates to a vector containing a DNA encoding CF6 or a polypeptide which is a part thereof, a transformant having been transformed by this vector, a method of efficiently producing CF6 and a partial polypeptide thereof, an antibody reacting specifically with CF6, a method for producing the antibody, and a method of assaying CF6.

BACKGROUND ART

Prostanoids produced via the arachidonate cascade (prostaglandin (PG), thromboxane (TG), leukotriene (LT), etc.) are physiologically active substances which are essential in maintaining the homeostasis in vivo. Prostacyclin ($PGI_2$), which is a prostanoid is synthesized in hemoendothelial cells under the action of $PGI_2$ synthase on $PGH_2$ having been formed from arachidonic acid by cyclooxygenase and prostaglandin $H_2$ ($PGH_2$) synthase.

It is known that the $PGI_2$ has the following pharmacological effects:

(1) $PGI_2$ binds to $PGI_2$ receptor on membrane and activates adenyl cyclase to form cAMP, thereby exhibiting a platelet aggregation inhibitory effect and a vasodilating effect (Nakahata et al., Yakkyoku 50:1365–1373, 1999);

(2) $PGI_2$ plays an important role in thrombus formation caused by hemoendothelial disorder (Murata, T. et al., Nature 388:678–682, 1997); and (3) $PGI_2$ is a major prostanoid inducing inflammatory edema (Murata, T. et al., Nature 388:678–682, 1997).

As described above, the biosynthesis pathway of $PGI_2$ and the enzymes participating in its biosynthesis (arachidonate cascade) have been identified and thus the physiological activities of $PGI_2$ have been clarified to a certain extent. However, the mechanism of regulating the $PGI_2$ production in diseases still remains unknown.

Regarding the regulation of the $PGI_2$ production, on the other hand, it has been suggested from the results of experiments with the use of spontaneously hypertensive rats (SHR), that an endogenous $PGI_2$ production inhibitor may be present in SHR (Osanai, T. et al., Jpn. Circ. J. 54, 507–514, 1990; Falardeau, P. et al., Prostaglandins, 29, 621–628, 1985). Although this endogenous $PGI_2$ production inhibitor has not yet been discussed sufficiently, the present inventors successfully isolated and purified from a SHR heart a $PGI_2$ production inhibitory factor secreted by smooth muscle cells originating in SHR mesenteric artery. Further, they determined the structure of this factor and clarified that it is rat CF6 (hereinafter referred to as rCF6) which is one of the subunits of $H^+$ ATP synthase Referential Example 1).

Mammalian $H^+$ ATP synthase is present in the mitochondrial inner membrane and consists of at least 14 subunits. CF6, which is one of these subunits, consists of 76 amino acids. CF6 is synthesized as a peptide having 32 amino acids containing a mitochondrial transit sequence at the N-end (Higuchi, T. et al., Biochem. Biophys. Res. Commun. 178, 793–799, 1991).

The present inventors have established a method comprising expressing a chimeric protein from which rCF6 can be cut off by using factor Xa with the use of *Escherichia coli* as a host, and cutting off rCF6 from the chimeric protein followed by purification (Referential Example 2).

In addition, the present inventors have disclosed that the action point of the inhibition of the $PGI_2$ production by CF6 resides in the $PLA_2$ inhibition (Referential Example 3), in particular, in the $cPLA_2$ inhibition (Referential Example 4) (Osanai, T. et al., J. Biol. Chem. 273, 31778–31778, 1998). However, the relationships between CF6, which is an intracellular peptide, and diseases have not been known so far. Moreover, it still remains unknown as to how CF6 acts on hemoendothelium in vivo, namely, whether or not CF6 is present in the blood.

On the other hand, it has been clarified the following facts with respect to the functions of $cPLA_2$.

(1) $cPLA_2$ is essentially required in the production of prostaglandin $E_2$, leukotriene $B_4$ and leukotriene $C_4$ which are inflammatory mediators in the arachidonate cascade; and (2) a mouse lacking this enzyme shows a small infarcted area after tentatively ligating the middle cerebral artery and scarcely suffers from edema or nerve defect in the brain (Bonventre JV, T. et al. Nature 390:622–625, 1997).

Based on these facts, it is estimated that $cPLA_2$ inhibitors are usable as potent remedies for inflammation or remedies for brain infarction, etc. However, there has been found hitherto neither an efficacious remedy nor a method of screening a $cPLA_2$ inhibitor on the basis of the effects of CF6.

As described above, the biosynthesis and physiological effects of $PGI_2$, the physiological effects of $cPLA_2$ in the arachidonate cascade and the relations among $PGI_2$, $cPLA_2$ and CF6 have been gradually clarified. However, causes of diseases, in which $PGI_2$ located at the end of the arachidonate cascade and $cPLA_2$ located at the initial point thereof participate, have not been sufficiently clarified yet.

DISCLOSURE OF THE INVENTION

The present inventors have clarified that CF6 is present in rat blood and human blood and that CF6 is produced in hemoendothelial cells. They have also disclosed that the blood rCF6 level is elevated with an increase in blood pressure in the case of hypertension with the shortage of $PGI_2$; that the blood pressure further increases by administering rCF6 in this state; and that an anti-rCF6 antibody exerts a hypotensive effect in the case of hypertension with a high rCF6 level. Moreover, they have found that the blood CF6 level is elevated in the case of human acute heart infarction, namely, the blood CF6 level changes in human diseases too, thereby having completed the present invention.

Under the above-described circumstances, the present invention relates to a pharmaceutical composition for the prevention or the treatment of diseases caused by changes in the blood CF6 level, diseases associated with the excess or shortage of $PGI_2$ and diseases associated with the accentuation or attenuation of $cPLA_2$ function, and diagnostic methods and a diagnostic aid for judging the onset and progress of diseases based on the control of the blood CF6 level.

Accordingly, the present invention provides a pharmaceutical composition for the prevention or the treatment of diseases associated with an increase or a decrease in the CF6 level, diseases associated with an increase or a decrease in the $PGI_2$ level and diseases associated with the accentuation or attenuation of the $cPLA_2$ function. The pharmaceutical composition comprises, as the active ingredient, CF6 activators (for example, CF6, CF6 secretion-promoting substances and CF6 agonists) or CF6 inhibitors (for example, CF6 secretion-inhibiting substances and CF6 antagonists). The present invention also provides a method of measuring the blood CF6 level. The present invention still further provides a diagnostic method and a diagnostic aid for diseases associated with an increase or a decrease in the CF6 level.

Moreover, the present invention provides CF6 secretion accelerating substances, CF6 secretion inhibitory substances, CF6 agonists and CF6 antagonists which are the active ingredients of the pharmaceutical composition for the prevention or the treatment of the diseases as cited above. In addition, the present invention provides an anti-CF6 antibody which is usable as a reagent in the method of measuring the blood CF6 level or as a diagnostic aid in the diagnostic methods. The present invention further provides a vector containing a DNA encoding CF6, a transformant having been transformed by this vector, and a method of producing a CF6-like peptide. According to the present invention, an antibody reacting specifically with CF6 or a partial polypeptide thereof and a method for producing the same are provided.

Figure 1:
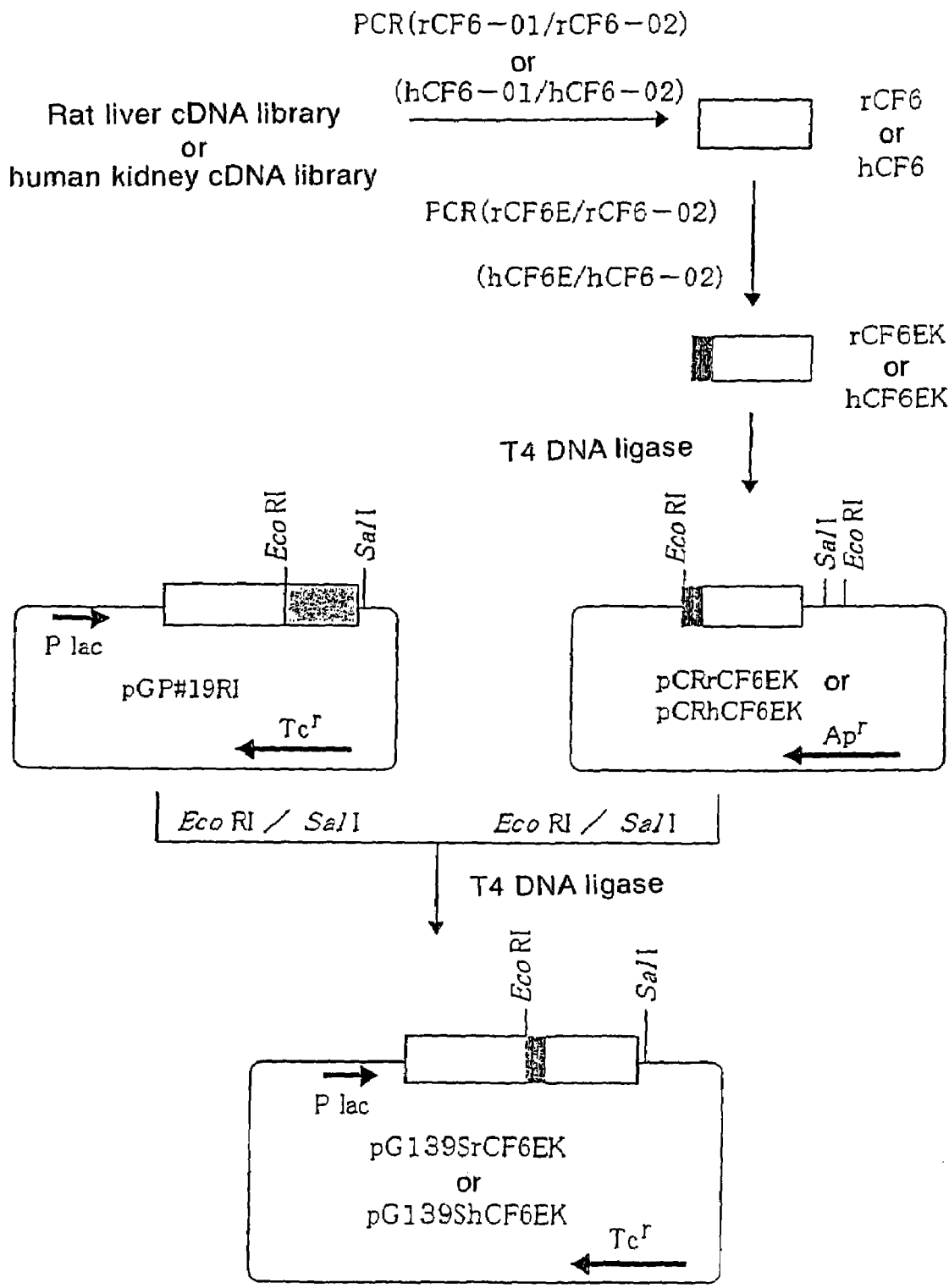
FIG. 1 is a diagram which illustrates how to construct a vector for expressing a chimeric protein from which rCF6 or human CF6 (hCF6) can be cut off with enterokinase from a rat liver cDNA library or a human kidney cDNA library.

MODE FOR CARRYING OUT THE INVENTION (Production of CF6)

In the present invention the rat CF6 and the human CF6, which are to be used as the active ingredients in the above-described pharmaceutical composition for the prevention or the treatment, as a reagent or a diagnostic aid in the method of measuring the blood CF6 level, or as a reagent or a diagnostic aid in the diagnostic methods for diseases associated with changes in the blood CF6 level, can be efficiently produced by using enterokinase as a cutting enzyme compared with the conventional method (Referential Example 2). Enterokinase is an enzyme which recognizes a sequence Asp-Asp-Asp-Asp-Lys (SEQ ID NO:3) and cuts the peptide bond at the C-end thereof. To obtain CF6, a chimeric protein carrying a protective peptide at the N-terminus of the enterokinase recognition sequence and CF6 or a partial peptide thereof at the C-terminus is obtained by a conventional gene recombination technique and then CF6 is cut off therefrom with enterokinase. As the chimeric protein, use can be made, for example, of a peptide wherein CF6 is bonded via the recognition sequence of enterokinase to the C-terminus of a peptide consisting of 139 N-terminal amino acids of *E. coli* β-galactosidase (cysteine residues at the 76- and 122-positions have been substituted by serine: SEQ ID NO:4). Due to a large accumulation of the insoluble fraction of *E. Coli*, this chimeric protein can be efficiently expressed and purified. After solubilizing the insoluble chimeric protein in a urea solution, CF6 can be cut off from the chimeric protein by treating with enterokinase. The thus cut off CF6 can be purified by subjecting to HPLC employing a C18 column. An expression vector can be constructed and a host can be transformed each by a conventional method well known by a person skilled in the art (Maniatitis et al., "Molecular Cloning: A Laboratory Manual", Cold Spring Harbor Laboratory, 1989).

(Partial Polypeptide)

The term "partial polypeptide" as used herein means a polypeptide corresponding to a part of CF6 which has an effect of inhibiting the production of $PGI_2$ from human umbilical venal endothelial cells (HUVEC). Also, polypeptides formed by the modification of a polypeptide corresponding to a part of CF6 by the deletion, addition, substitution or combination thereof of one to several amino acids and having an effect of inhibiting the production of $PGI_2$ from HUVEC fall within this category.

(Production of CF6 Antibody)

An antibody immunologically specific to CF6, which is to be used as the active ingredient in the above-described pharmaceutical composition for the prevention or the treatment or as a reagent or a diagnostic aid in the method of measuring the blood CF6 level or the diagnostic methods in the present invention, can be obtained by sensitizing an animal (preferably a non-human animal) with the use of CF6, its fragment or an analog thereof as an immunogen by a conventional experimental method. In case of preparing a monoclonal antibody, use can be made of, for example, the hybridoma method (Kohler, G. et al. Nature, 256:495–497, 1975) whereby an antibody produced by continuous cell line culture is presented. A single-stranded antibody against CF6 can be produced by applying a technique to be used in producing a single-stranded antibody (U.S. Pat. No. 4,946, 778). Also, a human-type antibody can be expressed by using a transgenic mouse having a human antibody production system (Green LL. et al. Nat Genet, 7, 13–21, 1994). In this specification, an example of the production of a polyclonal antibody, wherein rabbits were immunized with an antigen obtained by synthesizing a peptide having a cysteine added to the N-terminus of an rCF6- or hCF6-origin fragment consisting of about 20 amino acids and bonding keyhole limpet hemocyanin thereto via the N-terminal cysteine, is presented (Example 2).

(Method of Measuring CF6 Level)

According to the present invention, CF6 in a sample can be assayed by the RIA method or the ELISA method with the use of the antibody as described above (Radioimmunoassay: Kitagawa p. 79–88; Enzyme Immunoassay:p. 88–99, Shinseikagaku Jikken Koza 12, Bunshi Menekigaku III, Kogen, Kotai, Hotai, ed. by Nippon Seikagaku Gakkai, 1992). As an example thereof, an antagonistic inhibition system (RIA method) wherein quantification is carried out by inhibiting the reaction between a $^{125}$I-labeled antigen with an antibody by an antigen in a sample is presented in this specification (Example 2).

(Method of Screening CF6 Secretion Accelerating Substance or CF6 Secretion Inhibitory Substance)

According to the present invention, it is also possible to obtain a CF6 secretion accelerating substance or a CF6 secretion inhibitory substance by using the above-described method of measuring the CF6 level. More particularly speaking, a test substance is added to a liquid culture of cells capable of secreting CF6 (for example, HUVEC) and the amount of CF6 secreted into the liquid culture is measured by an assay system with the use of the anti-CF6 antibody (for example, the RIA method as described above). Thus, a CF6 secretion accelerating substance or a CF6 secretion inhibitory substance can be obtained (Example 7). It is still preferable to use cells causative of diseases as the cells capable of secreting CF6.

(Method of screening CF6 Agonist or CF6 Antagonist)

According to the present invention, it is also possible to obtain a method of detecting a CF6 agonist or a CF6 antagonist.

More particularly speaking, a test substance is added together with CF6 to a liquid culture of cells wherein the $PGI_2$ production is inhibited by CF6 (for example, HUVEC or smooth muscle cells originating in rat mesenteric artery). Then 6-keto-PGF1α, which is the stable metabolite of $PGI_2$, secreted in the liquid culture is quantitated. Thus, a CF6 antagonist causing an increase in the 6-keto-PGF1α amount or a CF6 agonist causing a decrease in the 6-keto-PGF1α amount can be obtained. Alternatively, an antagonist or an agonist can be detected by adding a test substance together with CF6 to a liquid culture of HUVEC in the presence of labeled arachidonic acid and measuring arachidonic acid thus released into the medium. It is still preferable to use cells causative of diseases as the cells producing $PGI_2$.

(Method of Identifying CF6-Binding Receptor)

The present invention also provides a method of identifying a CF6-binding receptor. A CF6-binding receptor can be identified by standard receptor-binding methods commonly known in the art with the use of CF6. Although these methods include the ligand binding method and the crosslinking assay method, the present invention is not restricted thereto. In such a method, CF6 is fused with a peptide sequence appropriate for radioisotope (for example, $^{125}$I) labeling, chemical modification (for example, biotinylation), detection or purification and then incubated with a membrane fraction of cells such as HUVEC. The labeled CF6 is also usable in the method of identifying a CF6 agonist or a CF6 antagonist in competition with the binding of CF6 to its receptor with the use of binding assay. Standard methods for carrying out such assays are well known in the art.

(Examples of Diseases)

The term "diseases associated with the excess of CF6" as used herein means diseases wherein the function of CF6 in the blood is accentuated to a level undesirable for a living body. Namely, these diseases are not always restricted to those wherein the blood CF6 level is higher than the level of normal persons. Namely, diseases associated with the shortage of $PGI_2$ and diseases associated with the attenuation of the $cPLA_2$ function or the $cPLA_2$ hypofunction fall within this category. Examples thereof include diseases associated with accentuated platelet agglutination, diseases associated with peripheral circulatory failure caused by inhibited vasodilatation, heart infarction, angina pectoris, heart failure, pulmonary hypertension, hypertension, cerebrovascular disorder, arteriosclerosis obliterans, arteriosclerosis, hyperlipemia, diabetes, bronchial disease, stomach ulcer, eclampsia of pregnancy, hemolytic-uremic syndrome and thrombotic thrombocytopenic purpura.

The term "diseases associated with the shortage of CF6" as used herein means diseases wherein the function of CF6 in the blood is attenuated to a level undesirable for living body. Namely, these diseases are not always restricted to those wherein the blood CF6 level is lower than the level of normal persons. Namely, diseases associated with the excess of $PGI_2$ and diseases associated with the accentuation of the cPLA$_2$ function or cPLA$_2$ hyperfunction fall within this category. Examples thereof include brain infarction, acute pancreatitis, asthma, ARDS and rheumatoid arthritis.

(Provision of Pharmaceutical Compositions for Treatment)

According to the present invention, the pharmaceutical composition for the treatment of the above-described diseases associated with the excess or shortage of the blood CF6 level can be provided.

In case where the CF6 activity is in excess, the CF6 activity can be lowered by administering antagonists or CF6 secretion inhibitory substances in an amount efficacious in inhibiting the action of CF6 on ligands, substrates, receptors, enzymes, etc. These antagonists or CF6 secretion inhibitory substances can be obtained by the screening method as described above.

To treat abnormal conditions associated with the shortage of CF6, on the other hand, the CF6 activity can be elevated by administering agonists or CF6 secretion accelerating substances in an amount efficacious in promoting the action of CF6 on ligands, substrates, receptors, enzymes, etc. These agonists or CF6 secretion accelerating substances can be obtained by the screening method as described above.

(Method of Producing Preparations)

Medicinal preparations of the CF6 secretion accelerating substances, CF6 secretion inhibitory substances, CF6 agonists or CF6 antagonists obtained by using the screening method according to the present invention can be produced by conventional methods. For example, these preparations may be used in the dosage form of solid preparations such as optionally coated tablets, capsules, granules or fine powder; injections, eye drops or nasal drops obtained by dissolving in water or other pharmaceutically acceptable liquid vehicles; or external preparations such as ointments or patches.

These preparations can be produced in a conventional manner with the use of additives commonly employed in the art. In case of the production of solid preparations for oral administration such as tablets, capsules, granules and fine powder, use can be made as additives of: (1) fillers such as lactose, starch and crystalline cellulose; (2) binders such as hydroxypropylcellulose and polyvinyl pyrrolidone; (3) disintegrating agents such as starch and croscarmellose sodium; (4) plasticizers such as macrogol and triethyl citrate; (5) lubricants such as magnesium stearate and talc; (6) coating bases such as hydroxypropylmethylcellulose and Eudragit; (7) taste correctives such as sucrose and mannitol; and odor correctives, coloring agents, etc.

In case of the production of injections, eye drops and nasal drops, use can be made as additives of: (1) tonicity agents such as sodium chloride, D-mannitol and D-sorbitol; (2) pH controlling agents such as hydrochloric acid and citric acid; (3) buffers such as sodium citrate, sodium acetate and boric acid; (4) soothing agents such as procaine hydrochloride; and stabilizers, surfactants, etc. Considering the stability, etc. of the active ingredient, these preparations may be either dissolved or suspended just before using or in the form of solutions.

In case of the production of external preparations such as ointments and patches, use can be made as additives of: (1) bases such as liquid paraffin, vaseline and hydrophilic ointment; (2) emulsifiers such as polysorbate 80 and tragacanth; (3) preservatives such as sodium benzoate and propyl parahydroxybenzoate; (4) soothing agents such as procaine hydrochloride; and stabilizers, surfactants, etc.

The preparations thus prepared are packaged in an appropriate manner depending on the dosage form. Examples of the package styles include bottling, folding, PTP-packaging, ampul-filling and vialling. The preparations thus obtained can be administered to, for example, mammals such as rat, rabbit, sheep, pig, cow, cat, dog, monkey, humans, etc. The administration dose varies depending on the indication, symptom, administration route, etc. In case of a human adult weighing 60 kg, the daily dose generally ranges from about 0.01 to 300 mg, preferably from about 0.1 to 100 mg. In case of other animals, the administration dose may be calculated by converting the bodyweight into a corresponding fraction of 60 kg.

(Diagnostic Methods)

The present invention also provides methods of diagnosing diseases associated with an increase or a decrease in the CF6 level which comprises measuring the CF6 level in collected blood samples. As described above, the CF6 level can be measured by the RIA method or the ELISA method with the use of antibody.

(CF6 Gene or mRNA)

According to the present invention, it is possible to use a CF6 gene or mRNA usable as a diagnostic or a diagnostic aid for the underexpression or hyperexpression of CF6, changes in the localization of CF6 or diseases caused thereby.

Individuals having a mutated CF6 gene can be detected by various methods for measuring DNA sequences. The nucleic acids to be employed in the diagnosis can be obtained from the sample cells present in, for example, blood, urine, saliva, biopsy specimens or autopsy specimens. Genomic DNA may be either employed as such or amplified prior to the analysis by the PCR method or the like. mRNA or cDNA may be used in the same manner. Thus, a deletion or insertion can be detected based on the difference in the amplification product size from the normal genotype. A point mutation can be identified by hybridizing the amplified DNA with CF6 DNA having the normal DNA nucleotide sequence. Completely matched sequences can be distinguished from sequences of mismatched double strands by digesting with RNase or by measuring difference in melting temperature. Also, a difference of DNA sequences can be detected based on a change in the mobility in gel when a DNA fragment is electrophoresed alone or together with a denaturing substance. It is also possible to detect the difference by directly determining the DNA sequence. A change in the sequence at a specific position can be clarified by a nuclease protective assay, for example, protection with RNase and S1 or by the chemical cutting method. Alternatively, it is also possible to construct an array of oligonucleotide probes containing the CF6 nucleotide sequence or fragments thereof and carry out, for example, an effective screening of a genetic mutation. This array method, which has been widely known, is applicable over a broad scope and is usable in studying various problems in the field of molecular genetics such as gene expression, genetic linkage and genetic change.

EXAMPLES

Now, the invention will be illustrated in greater detail by reference to the following Examples. However, it is to be understood that these Examples merely provide modes for carrying out the present invention and the invention is not to be construed as being limited thereto. Unless otherwise noted, technical terms and abbreviations are employed in these Examples in accordance with the common usage in the art. The plasmids, *E. Coli* and fundamental expression procedures employed in common in these Examples will be illustrated below for reference. To confirm and illustrate the prior art providing the basis of the present invention and the related art of the present invention, Referential Examples will be also given.

Figure 4:
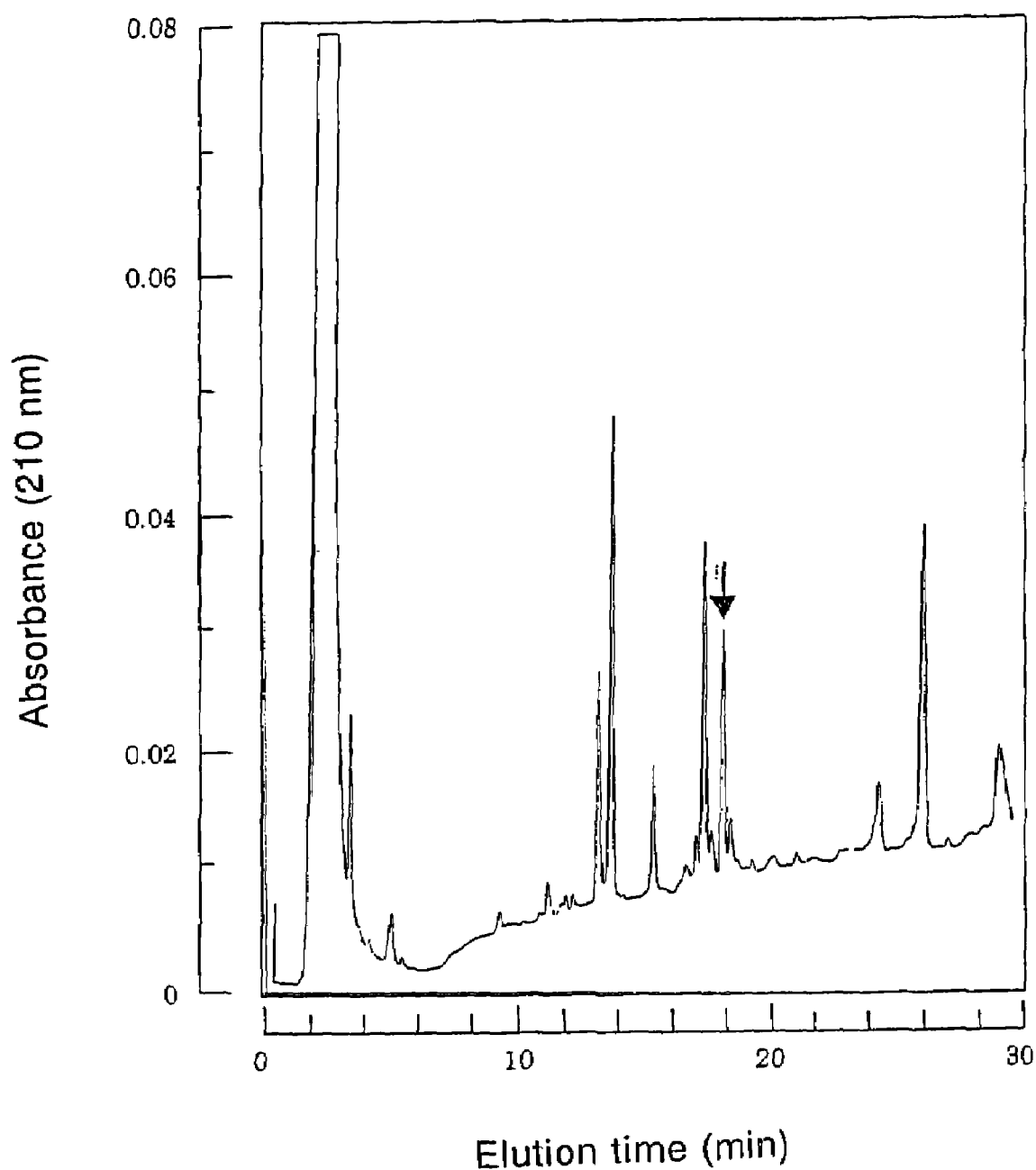
FIG. 4 shows the C18-HPLC elution profile of a solution wherein the hCF6-containing chimeric protein thus expressed is treated with enterokinase.

(Plasmid)

pG97S4DhCT[G] is a plasmid capable of expressing a chimeric protein wherein hCT[G] (a peptide having Gly added to the C-terminus at the 32-position of human calcitonin) is bonded via a sequence Glu-Phe-Glu to a peptide consisting of the amino acids from the N-terminus to the 97-position of β-galactosidase (called βGal-97S4D represented by SEQ ID NO:5 wherein Cys at the 76-position is substituted by Ser and Glu at the 40-, 41–71- and 75-positions are substituted by Asp) by an *E. coli* lactose operon promoter. A transformant obtained by using this plasmid can be selected depending on resistance to tetracycline. A chimeric protein with βGal-97S4D can be expressed by transferring an EcoRI-SalI DNA fragment consisting of the DNA domain encoding a target peptide and the coding frame. An *E. coli* W3110 strain containing this plasmid was named *Escherichia coli* SBM323 and deposited with National Institute of Bioscience and Human Technology, Agency of Industrial Science and Technology under the accession number FERMBP-3503 on Aug. 8, 1991.

pGP#19RI is a plasmid wherein a gene encoding the chimeric protein βGal-97S4D/hCT[G] of pG97S4DhCT[G] is substituted by another gene encoding a chimeric protein βGal-139S(SEQ ID NO:4)/hProPTH. A chimeric protein with βGal-139S can be expressed by transferring an EcoRI-SalI DNA fragment consisting of the DNA domain encoding a target peptide and the coding frame. This plasmid pGP#19RI can be constructed by inserting the EcoRI site into the DNA domain encoding the bond between the protective peptide βGal-139S and ProPTH of a plasmid pGP#19 (unexamined published Japanese application (Kokai) No.9-296000; FIG. 4).

A plasmid pCRII was purchased from Invitrogen Co. in the state of allowing direct linkage to DNA fragments having been amplified by the PCR method with the use of Taq DNA polymerase. A transformant obtained by using this plasmid pCRII can be selected depending on resistance to ampicillin.

(*E. coli* and Media)

The *E. coli* JM109 strain was purchased form Toyobo Co., Ltd. and employed in preparing the plasmids and expressing the chimeric proteins.

The media employed were an LB medium (0.5% (w/v) of yeast extract, 1% (w/v) of trypton, 0.5% (w/v) of NaCl) and an SB medium (2% (w/v) of yeast extract, 1% (w/v) of trypton, 0.5% (v/v) of glycerol, 1.2% (w/v) of $K_2HPO_4$, 0.3% (w/v) of $KH_2PO_4$).

(Fundamental Experimental Procedures)

Unless otherwise stated in particular, the following experimental procedures were employed in Examples. DNA nucleotide sequences were determined by using the dideoxy method with a DNA Sequencer 373 (Applied Biosystems). To cleave DNA with restriction enzymes, the reaction was performed for 1 hour using the enzymes in an amount 3 to 10 times more than the amount specified by the manufacturer. Plasmid structures were analyzed in 20 μL of a liquid reaction mixture by using 0.5 to 1 μg of DNA. Preparation of DNA was carried out in 50 to 100 μL of a liquid reaction mixture by using 3 to 10 μg of DNA. The reaction conditions (temperature, buffer, etc.) were set up in accordance with the manufacturer's instruction. The obtained DNA fragments were separated by agarose gel electrophoresis and subjected to analysis or preparation.

Samples for the agarose gel electrophoresis were prepared by adding 1.5 times by volume as much a colorant solution (15% (w/v) aqueous solution of Ficoll containing 0.25% (w/v) of Bromophenol Blue) to liquid reaction mixtures. As the buffer for the agarose gel electrophoresis, use was made of a TAE buffer (10 mM of tris, 20 mM of acetic acid, 2 mM of EDTA.Na, pH 6.8). In analyzing the plasmid structures and preparing the DNA fragments, migration was carried out by using Mupid-2 (COSMO BIO) at 100 V for 1 hour. The gel was stained with an aqueous solution of ethidium bromide (0.5 μg/ml) for 20 minutes and then irradiated with ultraviolet light to detect DNA bands. The concentration of the agarose gel was adjusted to 1.0, 1.5 and 2.0% (w/v) depending on the size of the DNA fragment to be fractionated. DNA in the agarose gel was extracted from the gel by using SUPREC-01 (Takara Shuzo Co., Ltd.). DNA solutions were treated with phenol and then subjected to precipitation from ethanol. Ligation reactions were carried out by using 0.05 to 1 μg of DNA fragments with the use of a TAKARA Ligation Kit (Takara Shuzo Co., Ltd.).

*E. Coli* was transformed by the calcium chloride method, wherein competent cells of JM109 strain were employed, and transformants were selected depending on the resistance to drugs (ampicillin or tetracycline).

The SDS polyacrylamide gel electrophoresis (SDS-PAGE) was performed in accordance with Laemmli's method (Laemmli et al. Nature 227, 680–685, 1970). Namely, ¼ times by volume as much 4×SDS sample buffer (375 mM of tris hydrochloride (pH 6.8), 30% (v/v) of glycerol, 7% (w/v) of SDS, 15% (v/v) of 2-mercaptoethanol and 0.1% (w/v) of Bromophenol Blue) was added to a sample and heated to 95° C. for 5 minutes. Then 10 μL of the reaction mixture was subjected to SDS-polyacrylamide gel (55 mm×85 mm×1 mm, Tefco) and electrophoresed at 20 mA for 80 minutes. After the completion of the electrophoresis, the gel was stained with a staining solution (10% (v/v) of acetic acid, 40% (v/v) of methanol and 0.25% (w/v) of Coomassie Brilliant Blue R250).

In the analysis and purification of peptides by HPLC with the use of a C18 column, use was made of an HPLC LC10A (Shimadzu Corporation) connected to an YMC0ODS-A302 column (diameter: 4.6 mm×150 mm), an YMC-ODS-A323 column (diameter: 10 mm×250 mm) (YMC K.K.) and an Inertsil ODS-2 C18 column (diameter: 4.6 mm×250 mm) (GL Science K.K.). Development was carried out under concentration gradient of a solution A (0.1% (v/v) trifluoroacetic acid (TFA)) and a solution B (0.092% (v/v) TFA/80% (v/v) acetonitrile, or 0.092% (v/v) TFA/60% (v/v) acetonitrile) at a flow rate of 1 ml/min or 2.5 ml/min. The peak area of the absorbance at 210 nm was measured.

DNA oligomers were synthesized by Greiner Japan or Lifetech Oriental.

The activity of inhibiting the $PGI_2$ production was evaluated by measuring the stable metabolite of $PGI_2$ (6-keto-PGF1α) secreted into the medium of smooth muscle cells collected from SHR mesenteric artery or human umbilical venal endothelial cells (HUVEC). Namely, the smooth muscle cells collected from SHR mesenteric artery were subcultured in a Dulbecco's modified Eagle medium (DMEM) containing 10% (v/v) of fetal calf serum until these cells attained the confluent state. HUVEC were proliferated in a synthetic medium (HuMedia, Kurabo Industries) containing 2% (v/v) of fetal calf serum, 10 ng/ml of EGF, 5 ng/ml of bFGF, 1 μg/ml of hydrocortisone and 10

µg/ml of heparin. The smooth muscle cells collected from SHR mesenteric artery or HUVEC were incubated for 30 minutes in the DMEM medium containing the sample to be analyzed and 6-keto-PGF$_{1\alpha}$ secreted into the medium during the incubation period was determined.

Blood pressure was measured in the open manner by inserting catheters directly into the aorta of rats anesthetized with 75 mg/kg of ketamine and 15 mg/kg of xylazine hydrochloride. Namely, two polyethylene catheters filled with physiological saline containing 20 U/ml of heparin were inserted respectively into the left carotid artery and the left femoral vein. Then the catheter inserted into the left carotid artery was connected to a pressure detector (Carrier Amplifier AP-601G, Nihon Kohden Co.). Each sample was dissolved in 200 µL of physiological saline and then administered via the vena cava.

The instruments and reagents were each used in accordance with the manufacturer's instruction. Fundamental gene manipulation procedures were carried out by reference to Maniatitis et al., "Molecular Cloning: A Laboratory Manual", Cold Spring Harbor Laboratory, 1989).

Example 1

Preparation of CF6 by Chimeric Protein Expression Method-1

Next, a method of producing CF6 by using enterokinase as an enzyme for cutting it off from a chimeric protein will be described in detail.

(Preparation of rCF6 cDNA and hCF6 cDNA)

rCF6 cDNA was obtained by the PCR method with the use of rat liver cDNA (Quick Clone cDNA Library, Clontech) as a template and rCF6-01 (SEQ ID NO:6) and rCF6-02 (SEQ ID NO:7) as primers. Namely, by using KOD (Toyobo Co., Ltd.) as a thermostable DNA polymerase, a liquid reaction mixture comprising 1 µL of the rat liver cDNA library, 5 µL of 10×reaction buffer, 7.5 µL of 2 mM of dNTP mix, 0.5 µL of rCF6-01, 0.5 µL of rCF6-02 and 35 µL of sterilized water was subjected to the reaction for 30 cycles with each cycle consisting of 30 seconds at 96° C., 1 minute at 56° C. and 40 seconds at 74° C. Thus rCF6 cDNA was obtained. Similarly, hCF6 cDNA was obtained by the PCR method with the use of human kidney cDNA (Quick Clone cDNA Library, Clontech) as a template and hCF6-01 (SEQ ID NO:8) and hCF6-02 (SEQ ID NO:9) as primers. The reaction conditions were as in the case of the rat.

SEQ ID NO:6 5'-ATGACTGTTCAGAGGATCTTCAG-3'

SEQ ID NO:7 5'-GTCGACTCAGGACTGGGGTTTGTCGAG-3'

SEQ ID NO:8 5'-ATGATTCTTCAGAGGCTCTTCAG-3'

SEQ ID NO:9 5'-GTCGACTCAGGCCTGGGGTTTTTCGATG-3'.

The rCF6 cDNA and hCF6 cDNA thus obtained were each electrophoresed on a 1.5% (w/v) agarose gel, collected by using SUPREC-01 (Takara Shuzo Co., Ltd.) and then used as a template for constructing a chimeric protein gene from which rCF6 or hCF6 could be cut off respectively with enterokinase.

(Preparation of rCF6 and hCF6 Having Enterokinase Recognition Sequence Added Thereto)

To construct the chimeric protein gene from which rCF6 or hCF6 could be cut off with enterokinase, a DNA oligomer having a gene sequence encoding Asp-Asp-Asp-Asp-Lys and a restriction enzyme EcoRI recognition site in the 5' side of a gene encoding the N-terminal side of rCF6 or hCF6 was synthesized (rCF6E: SEQ ID NO:10 and hCF6E: SEQ ID NO:11).

SEQ ID NO:10

5'-GAATTCGACGATGACGATAAGAATAAG-GAACTTGATCCTGTACAG-3'

SEQ ID NO:11

5'-GAATTCGACGATGACGATAAGAATAAG-GAACTTGATCCTATACAGA-3'.

The DNA sequence of SEQ ID NO:10 was transferred by the PCR method with the use of the rCF6 cDNA as a template and rCF6E (SEQ ID NO:10) and rCH6-02 (SEQ ID NO:7) as primers. As the thermostable DNA polymerase in PCR, use was made of Taq DNA Polymerase (Pharmacia). Namely, a liquid reaction mixture comprising 1 µL of rCF6 cDNA, 5 µL of 10×reaction buffer, 8 µL of 1.25 mM of dNTP mix, 0.5 µL of rCF6-01, 0.5 µL of rCF6-02 and 25 µL of sterilized water was subjected to the reaction for 8 cycles with each cycle consisting of 1 minutes at 96° C., 1 minute at 60° C. and 30 seconds at 72° C. Thus rCF6 cDNA having the enterokinase recognition sequence and the restriction enzyme EcoRI recognition sequence in the 5'-side was obtained. The DNA fragment thus amplified was cloned into pCRII (pCRrCF6EK) and the nucleotide sequence was confirmed. Similarly, the DNA sequence of SEQ ID NO:11 was transferred by the PCR method with the use of the hCF6 cDNA as a template and hCF6E (SEQ ID NO:11) and hCF6-02 (SEQ ID NO:9) as primers. The reaction conditions were as in the case of the rat. The DNA fragment thus amplified was cloned into pCRII (pCRhCF6EK) and the nucleotide sequence was confirmed.

(Construction of Chimeric Protein-Expression Vectors)

The plasmids pCRrCF6EK and pCRhCF6EK were cut with restriction enzymes EcoRI and SalI to give EcoRI-SalI DNA fragments rCF6EK and hCF6EK each consisting of 0.3 kb. These DNA fragments have DNA nucleotide sequences encoding proteins containing rCF6 or hCF6 having an enterokinase recognition sequence Asp-Asp-Asp-Asp-Lys (SEQ ID NO:3) bonded to the N-terminus and a restriction enzyme EcoRI site in the upstream thereof and another restriction enzyme SalI site in the downstream thereof. The plasmid pGP#19RI was cut with the restriction enzymes EcoRI and SalI and then a DNA fragment of about 3.5 kb containing the vector part was prepared. This DNA fragment was ligated to rCF6EK or hCF6KE, thereby giving plasmids pG139SrCF6EK and pG139ShCF6EK respectively.

(Expression and Purification of Chimeric Proteins)

The *E. coli* JM109 strain was transformed by using the plasmids pG139SrCF6EK and pG139ShCF6EK, thereby giving JM109[pG139SrCF6EK] and JM109[pG139ShCF6EK] respectively. JM109[pG139SrCF6EK] and JM109[pG139ShCF6EK] were each cultured in an SB medium containing 10 µg/mL of tetracycline under aeration and agitation at 37° C. with the use of a 3 L jar fermenter. 8 hours thereafter, IPTG was added to give a final concentration of 1 mM and the culture was continued overnight. 3 L of the liquid culture was centrifuged at 6,000 rpm at 4° C. for 10 minutes by using a centrifuge 20PR-52D (Hitachi, Ltd.) and then the cells were collected. The cells were suspended in 20 mM tris hydrochloride (pH 7.0) containing 0.5% (w/v) of Triton X-100, 1 mM EDTA and disrupted by ultrasonication. Then the disrupted cells were centrifuged at 6,000 rpm at 4° C. for 15 minutes by using a centrifuge 05PR-22 (Hitachi, Ltd.). Thus, the chimeric protein was collected in the precipitate fraction as an inclusion body. The dissolution and centrifugation of the precipitate fraction were repeated thrice to thereby give a partially purified chimeric protein. The hCF6 chimeric protein was prepared in the same manner.

(Cutting off of hCF6 and rCF6 from Chimeric Proteins and Purification)

As a method of cutting off rCF6 from a chimeric protein, the method with the use of factor Xa as a cutting enzyme may be cited (Referential Example 2). To solubilize the chimeric protein and treat it with the factor Xa in this method, it is necessary to use at least 2 M of urea. At this urea concentration, the activity of the factor Xa is lowered to 1/10. Therefore, it is necessary in this case to use a large amount of the factor Xa, i.e., 1/60 times as much as the chimeric protein. In addition, the factor Xa shows only a low substrate specificity in the presence of urea. As a result, the cutting efficiency from the chimeric protein was as low as about 8%.

Figure 2:
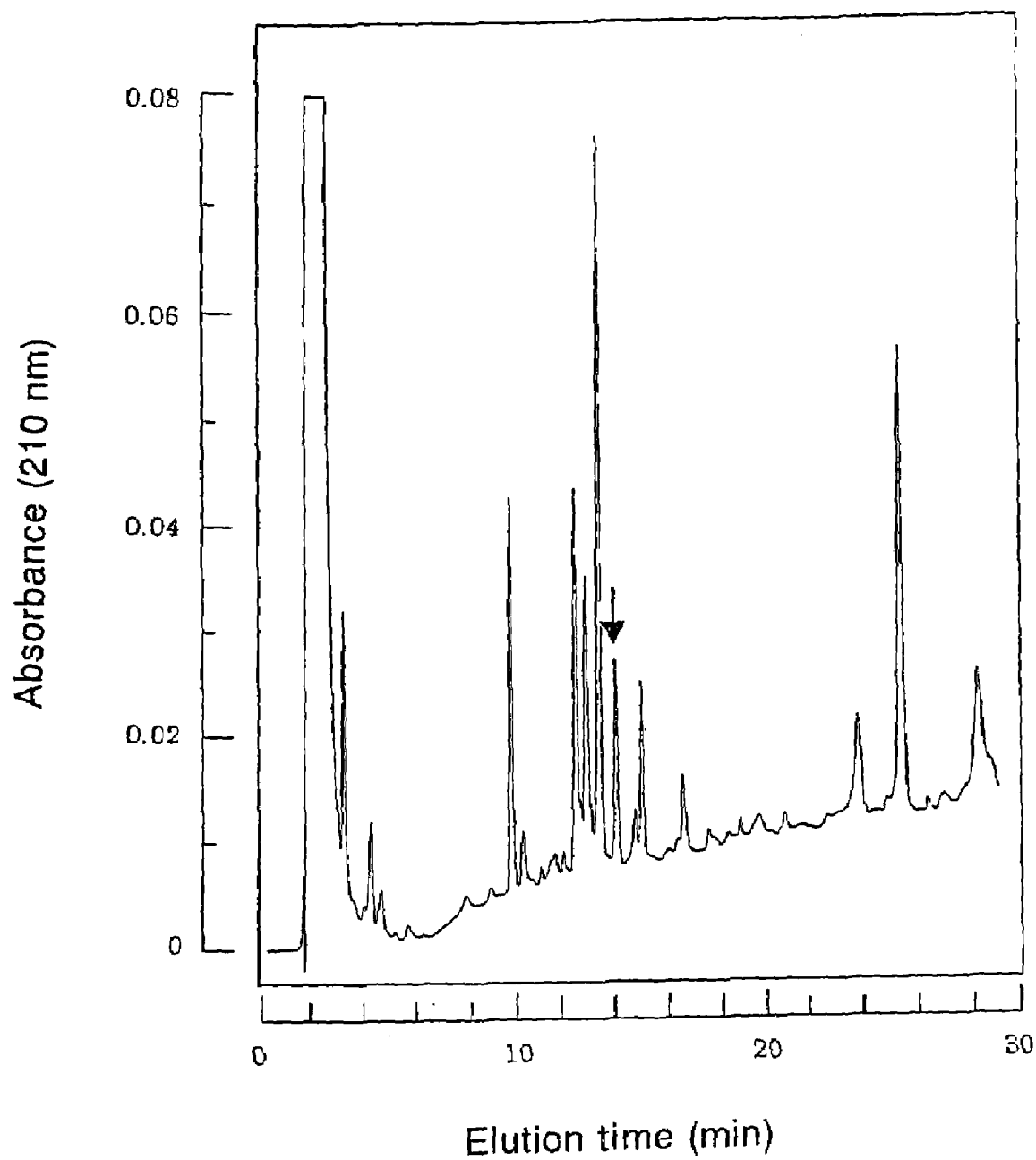
FIG. 2 shows the C18-HPLC elution profile of a solution wherein the rCF6-containing chimeric protein thus expressed is treated with enterokinase.

Therefore, attempts were made to elevate the CF6 cutting efficiency by using enterokinase as a cutting enzyme. First, 4 mg of the crude rCF6 chimeric protein was solubilized in 1.75 mL of a 10 M urea solution. Then, the obtained solution was centrifuged to thereby eliminate insoluble matters. To the supernatant, 0.5 mL of 10×EK buffer (200 mM of tris hydrochloride, (pH 8.0), 500 mM of NaCl, 20 mM of $CaCl_2$) and 30 U (about 3.4 μg, corresponding to about 1/1200 of the substrate) of enterokinase (Stratagene) were added and the total volume of the mixture was adjusted to 5 mL with distilled water. After reacting at 22° C. overnight, the liquid reaction mixture was poured into SepPak 18 (Waters) to thereby adsorb the peptides. The peptides thus adsorbed were eluted with an 80% (v/v) acetonitrile solution containing 0.1% (v/v) of TFA. The eluate was freeze-dried and then dissolved in 0.1% (v/v) TFA. A 1/10 portion thereof was subjected to HPLC connected to YMC-ODS-A302 (diameter: 4.6 mm×150 mm). Then a peak eluted about 14.2 minutes after loading the sample was collected as an rCF6 fraction (FIG. 2). The same procedure was repeated 10 times and the fractions thus eluted were combined, thereby giving partially purified rCF6.

Figure 3:
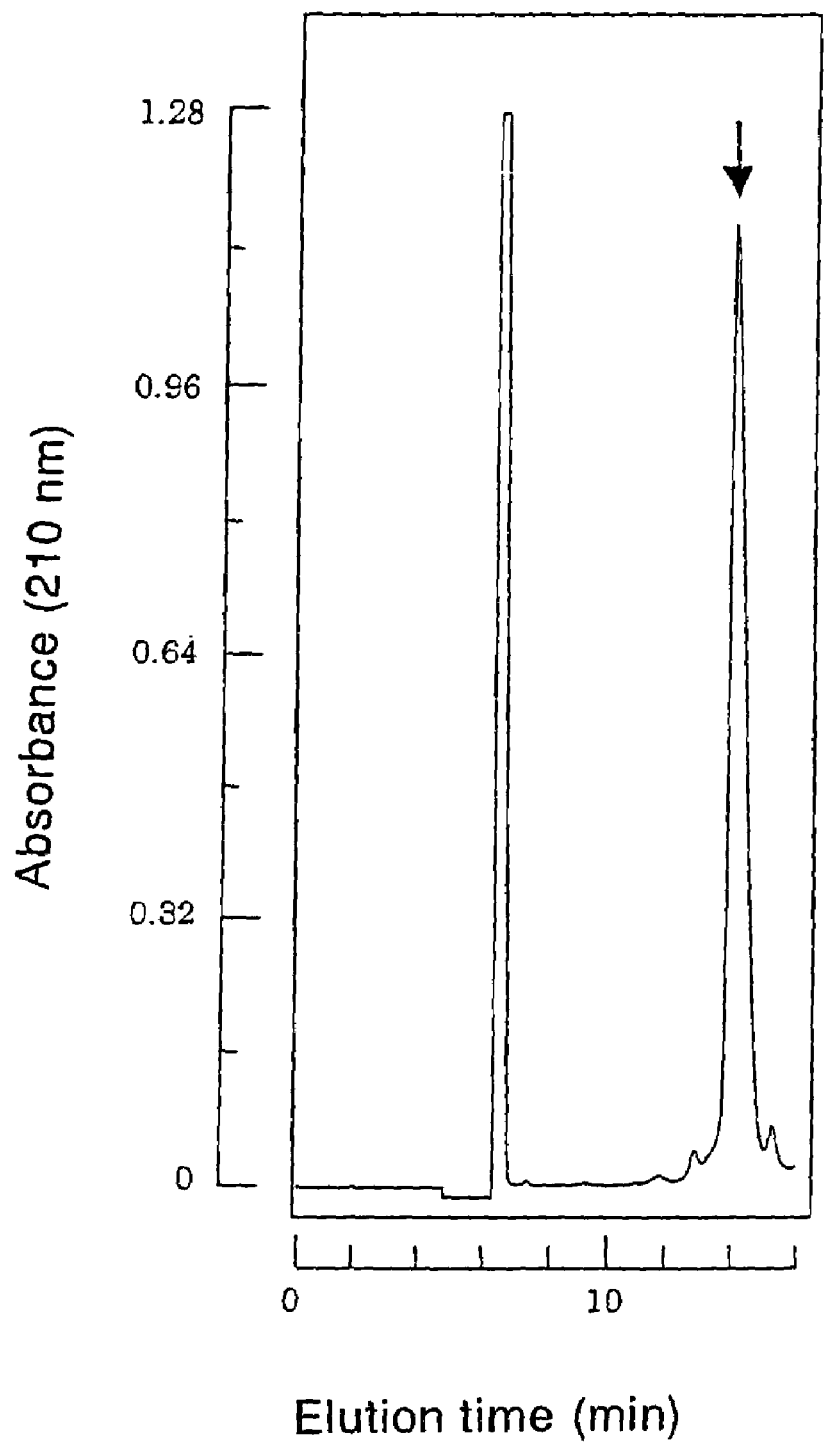
FIG. 3 shows the C18-HPLC elution profile of partial purified rCF6.
Figure 5:
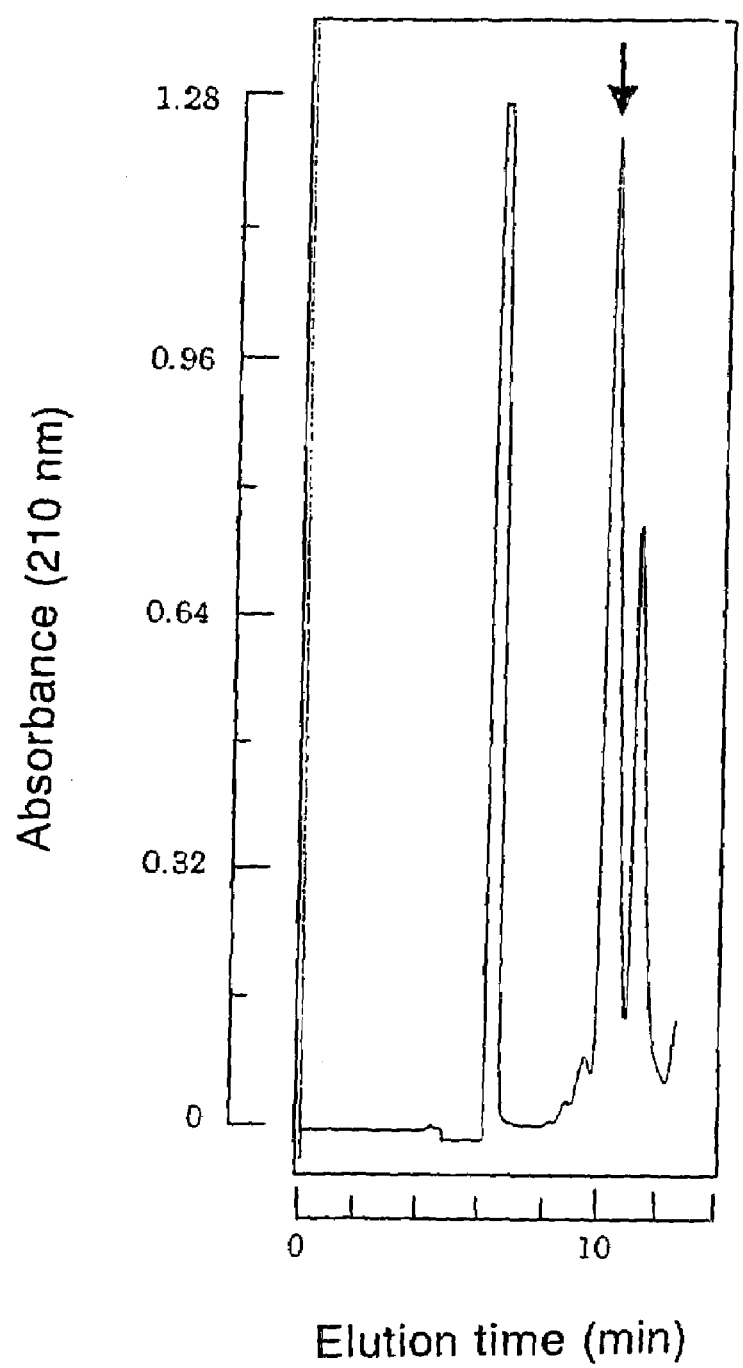
FIG. 5 shows the C18-HPLC elution profile of partial purified rCF6.
Figure 14:
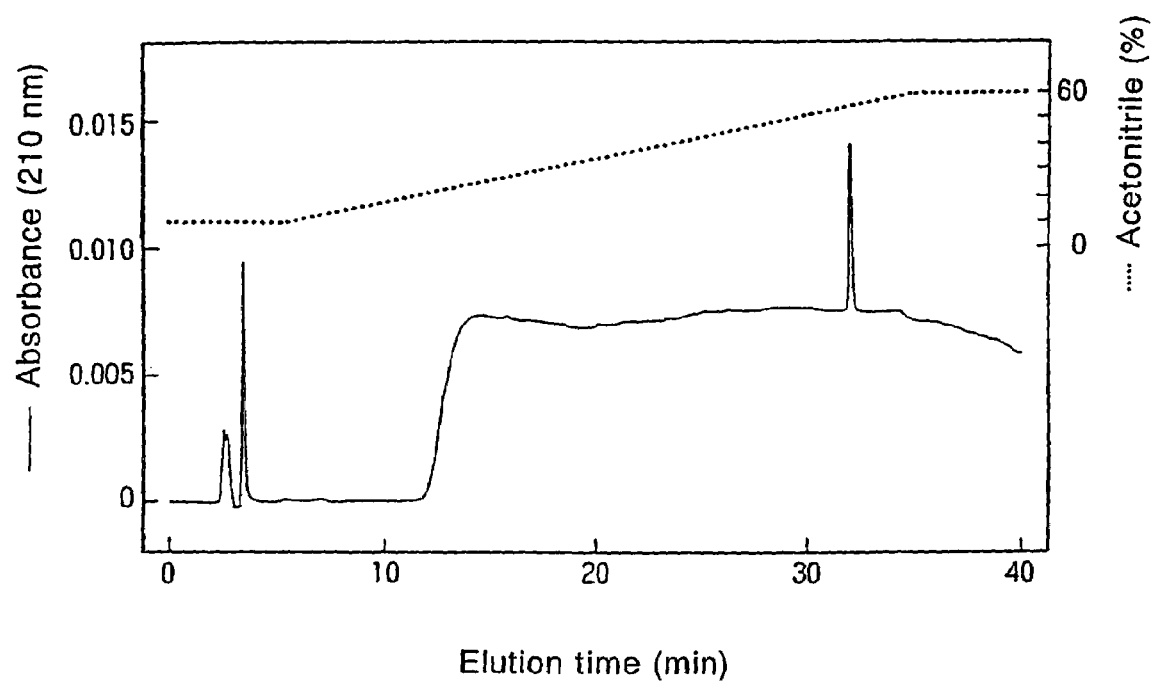
FIG. 14 provides a chart obtained by analyzing the active fraction in the above FIG. 13 by HPLC.

This partially purified rCF6 fraction was freeze-dried, then dissolved in 0.1% TFA and then purified by HPLC connected to YMC-ODS-AM-323 (FIG. 3, % B:40–43/18 min, flow rate: 2.5 ml/min). The peak eluted after about 14.2 minutes was collected and freeze-dried to give an rCF6 specimen. The structure of rCF6 was confirmed based on the facts that it showed a single peak in mass spectrometry with the use of a mass spectrometer MALDI-TOFMS (Voyager Elite: Nippon PerSeptive), that its molecular weight roughly agreed with the theoretical value, and that the 10 amino acids at the N-terminus were identical with those of rCF6, when analyzed by using an amino acid sequence analyzer PPSQ-10 (Shimadzu Corporation).

hCF6 was cut off from the chimeric protein and purified as in the case of rCF6. The hCF6 was eluted after about 18.0 minutes in the first HPLC (FIG. 14). In the chromatographic re-purification, it was eluted after about 10.5 minutes (FIG. 5, elution concentration gradient, % B:45–48/18 min). The structure was confirmed as in the case of rCF6.

About 210 μg and about 290 μg of hCF6 and rCF6 were respectively obtained from 400 mg portions of the chimeric proteins and the cutting efficiencies were about 15% and about 20% respectively. Namely, the cutting efficiencies were elevated 2 to 2.5-fold, compared with the case where the factor Xa was employed as the cutting enzyme (yield: 8%).

Example 2

Assay of CF6 in Rat Blood (Preparation of Antirat CF6 Rabbit Antibody (Anti-rCF6 Antibody))

A peptide consisting of 20 amino acids in total, wherein cysteine was added to the N-terminus of the 19 C-terminal amino acids of rCF6 (SEQ ID NO:2) (i.e., (CFPTFNFED-PKFEVLDKPQS:C-rCF6 (58–76):SEQ ID NO:12), was synthesized by the Fmoc solid phase method and purified by HPLC with the use of a C18 column. Then an antigen for immunization was prepared by bonding keyhole limpet hemocyanin (KLH) to the peptide thus synthesized via the N-terminal cysteine.

Figure 6:
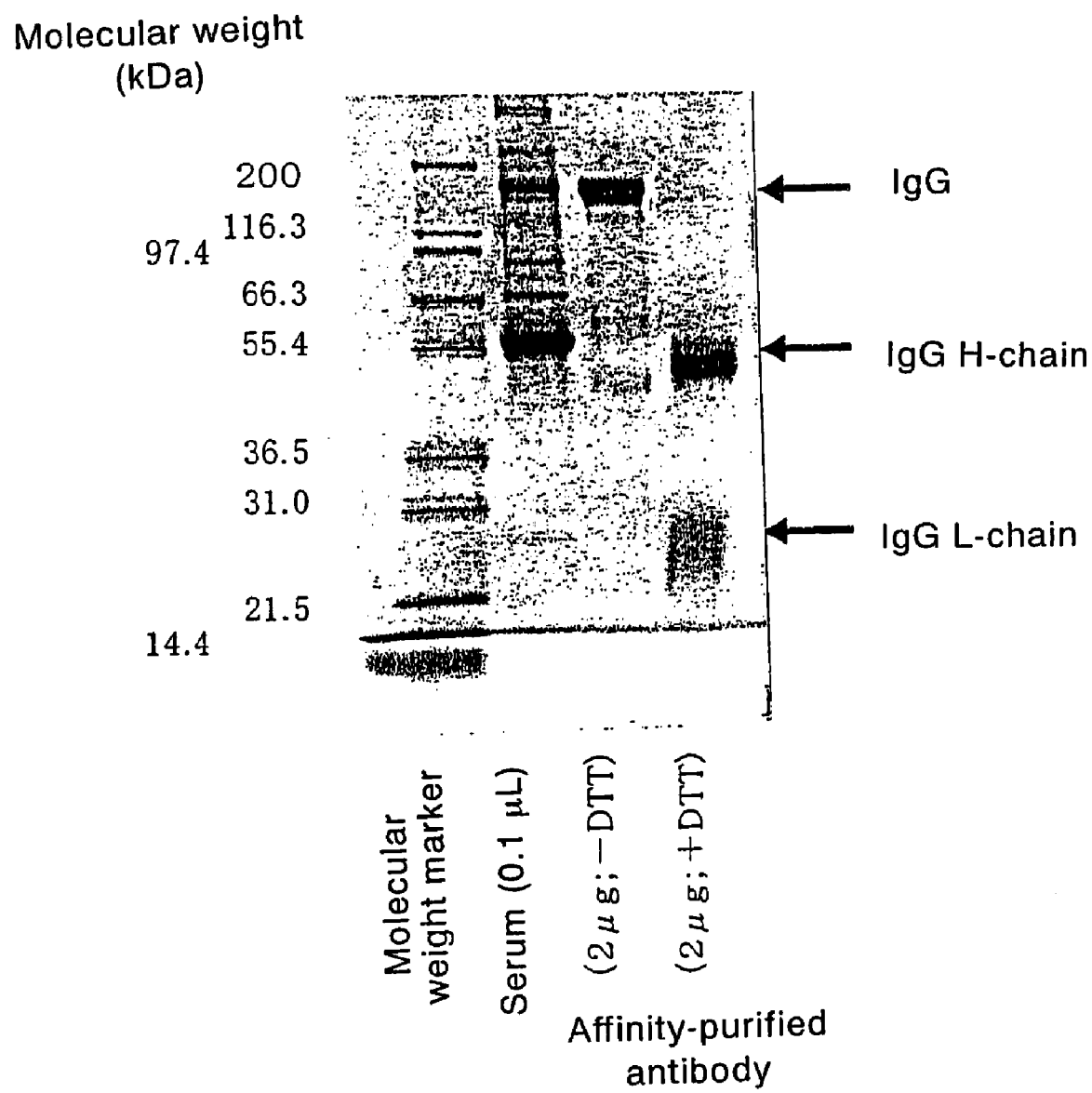
FIG. 6 provides SDS-PAGE patterns of an antiserum prepared by administering to rabbits an immune antigen derived from rCF6, and of antibodies purified by the immunoaffinity chromatograpy using an antigen peptide as the affinty ligand.

As animals, two female New Zealand white rabbits were employed. At the priming, the antigen emulsified with complete Freund's adjuvant (CFA) was subcutaneously administered at 4 positions of the dorsal part of the rabbits. 2, 6 and 8 weeks thereafter, the antigen emulsified with incomplete Freund's adjuvant (IFA) was administered in the same manner to thereby immunize the animals. Then all of the blood samples of the animals were collected and thus antisera were obtained. The antibody titers of the antisera were measured by ELISA with the immobilization of the antigen. The antibody titers of the rabbit sera before the immunization were each 50 or less, while the antibody titers of the antisera of the immunized rabbits were 59,600 and 81,400 respectively. The antibody was purified from the antisera by the immunoaffinity chromatograpy using an antigen peptide as the affinity ligand (FIG. 6). The antibody thus purified was concentrated, dialyzed against a PBS solution containing 0.1% (w/v) of $NaN_3$ and then stored at −80° C. until it was used.

(Setting up of Method of Measuring rCF6 Level)

A peptide consisting of 20 amino acid in total, wherein tyrosine was added to the N-terminus of the 19 C-terminal amino acids of rCF6 (SEQ ID NO:2) (i.e., (YFPTFNFED-PKFEVLDKPQS:Y-rCF6 (58–76):SEQ ID NO:13), was synthesized by the Fmoc solid phase method and purified by HPLC with the use of a C18 column. Y-rCF6(58–76) was labeled with radioactive iodine ($^{125}$I-labeling) by the lactoperoxidase method. The $^{125}$I-labeled Y-rCF6(58–76) was purified by HPLC with the use of a C18 column and then bovine serum albumin was added to give a final concentration of 0.1% (w/v). Then it was stored at −80° C. until it was used.

As the reaction system, use was made of an antagonistic system wherein the reaction between the $^{125}$I-labeled antigen and the antibody was quantified by inhibiting by the antigen in a sample. Namely, 100 μL of a sample containing 0.25 to 32 ng of rCF6 was mixed with 100 μL of the rCF6 antibody (diluted 2500-fold) and reacted for 12 hours. Then 100 μL (20,000 cpm) of the $^{125}$I-labeled Y-rCF6(58–76) was added thereto and the mixture was further reacted overnight. Next, 1 mL of antirabbit IgG goat serum (Japan Immunoresearch Laboratories Co., Ltd.) diluted 60-fold with RIA buffer (50 mM of $Na_2HPO_4$, 80 mM of NaCl, 25 mM of EDTA.2Na, 0.05% (w/v) of $NaN_3$, 0.5% (w/v) of bovine serum albumin, pH 7.4) containing 100 μL of 200 μg/mL rabbit IgG and 10% (w/v) of polyethylene glycol 6000 was added and the resultant mixture was allowed to stand for 1 hour. Then it was centrifuged at 3,000 rpm for 30 minutes and the supernatant was eliminated. The $^{125}$I level in the supernatant was measured with a gamma counter. These reactions were all carried out at 4° C. As a result, dose-dependent radioactivity was observed in the precipitate within the range of 0.25 to 16 ng/100 µL. Thus, a method of measuring the rCF6 level in a sample could be set up.

(Assay of rCF6 in Rat Blood)

By using the assay method as described above, measurement was made of rCF6 in the blood of male spontaneously hypertensive rats (SHR) and rats, 4 weeks of age, with normal blood pressure (WKY), and SHR and WKY of 16 weeks of age.

Each group had 5 animals. The blood of each animal was collected by using a cylinder containing a 1% (w/v) EDTA.2Na solution in 1/10 dose. The blood thus obtained was centrifuged under cooling to extract the plasma. The plasma was stored at −80° C. until the assay. 0.2 ml of 2 N hydrochloric acid was added to 0.8 ml of the plasma and the mixture was allowed to stand at 4° C. for 10 minutes. Next, it was centrifuged at 4° C. at 10,000 rpm for 30 minutes. The supernatant was added to a SepPak C18 column and washed with 5 ml portions of 0.1% (v/v) TFA thrice. After eluting from the column with 2 ml of a 60% (v/v) acetonitrile solution containing 0.1% (v/v) of TFA, the solvent was removed in vacuo and the residue was dissolved in 0.2 to 0.4 ml of RIA buffer to give a sample for RIA which was then used in the assay method with the use of the anti-rCF6 antibody as described above.

As the results of the assay of rCF6 in the plasma of the rats of each group, every group showed a plasma rCF6 level exceeding 200 pg/mL. At the age of 4 weeks, no difference was observed between the plasma rCF6 levels of SHR and WKY. At the age of 16 weeks, the plasma rCF6 level of SHR was significantly increased and thus higher than that of WKY ($p<0.05$) (Table 1).

Thus, it is clarified for the first time that rCF6 is present in rat blood. It is also found out that the blood rCF6 level increases with aging (i.e., the onset of hypertension) in the spontaneously hypertensive model (SHR) suffering from the shortage of $PGI_2$. That is to say, it is clarified that the onset of hypertension caused by the shortage of $PGI_2$ correlates to the blood CF6 level.

[Table 1]

TABLE 1

| | Plasma rCF6 level (pg/ml) | |
|---|---|---|
| Age | WKY | SHR |
| 4 weeks | 414 ± 123 | 216 ± 108 |
| 16 weeks | 294 ± 126 | 2310 ± 813 |

Expressed in mean ± standard error.

(Molecules in anti-rCF6 Antibody-Reactive Fraction of RIA Sample by HPLC)

Anti-rCF6 antibody was prepared by using an rCF6 fragment (58–76) as an antigen. Thus, the amount of CF6 measured in the above-described RIA system included the peptides containing the C-terminal fragment originating in rCF6. The RIA sample was fractionated by HPLC and the reactivity of anti-rCF6 antibody of each fraction was examined. The RIA sample was adsorbed by SepPak C18 and eluted with a 60% (v/v) acetonitrile solution containing 0.1% (v/v) of TFA. The sample thus eluted was freeze-dried, dissolved in 0.1% (v/v) TFA and separated and fractionated by HPLC connected to an Inertsil ODS-2 C18 column (diameter:4.6 mm×250 mm, GL Science K.K.) by washing with a 20% (v/v) acetonitrile solution containing 0.1% (v/v) of TFA for 5 minutes or longer and then eluting under linear gradient of acetonitrile (20–60%) for 30 minutes. Thus, it was confirmed that 90% or more of the antibody reactivity was eluted in the same fraction as rCF6 in the assay system with the use of the antid-rCF6 antibody as described above.

These results indicate that 90% or more of molecules reactive to the anti-rCF6 antibody present in the blood are not peptides containing the C-terminal fragment originating in rCF6 but rCF6 per se.

Example 3

Preparation of Anti-hCF6 Rabbit Antibody (Anti-hCF6 Antibody) and Construction of hCF6 Assay System Antisera against hCF6 were obtained as in Example 2 but using as an antigen for immunization a peptide consisting of 19 amino acid wherein cysteine was added to the N-terminus of the N-terminal amino acids (10–27) of hCF6 (SEQ ID NO:1) (i.e., CLFVDKIREYKSKRQTSGG:C-hCF6 (10–27), SEQ ID NO:14) bonded to KLH. The antibody titers of the immunized rabbits were 123,000 and 121,300. The anti-hCF6 antibody was purified as in Example 2. The hCF6 assay system was constructed as in the rCF6 assay system but using a peptide consisting of the N-terminal amino acids (10–27) of hCF6 (SEQ ID NO:2) (LFVD-KIREYKSKRQTSGG:hCF6(10–27), SEQ ID NO:15) as the $^{125}$I-labeled peptide and hCF6 as the standard.

Example 4

Effects of Anti-rCF6 Antibody on Rat Blood Pressure (Effects of Anti-rCF6 Antibody on Rat Blood Pressure)

Figure 7:
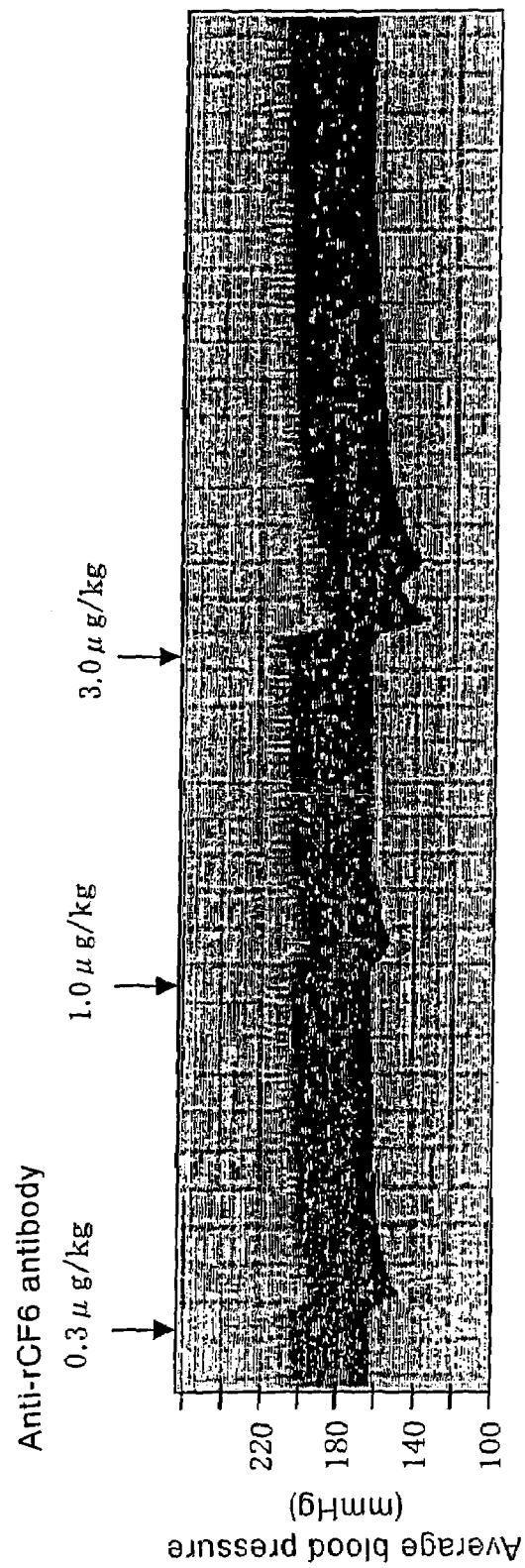
FIG. 7 provides a chart which shows the effect of the anti-rCF6 antibody on the blood pressure of SHR (16 weeks of age).
Figure 8:
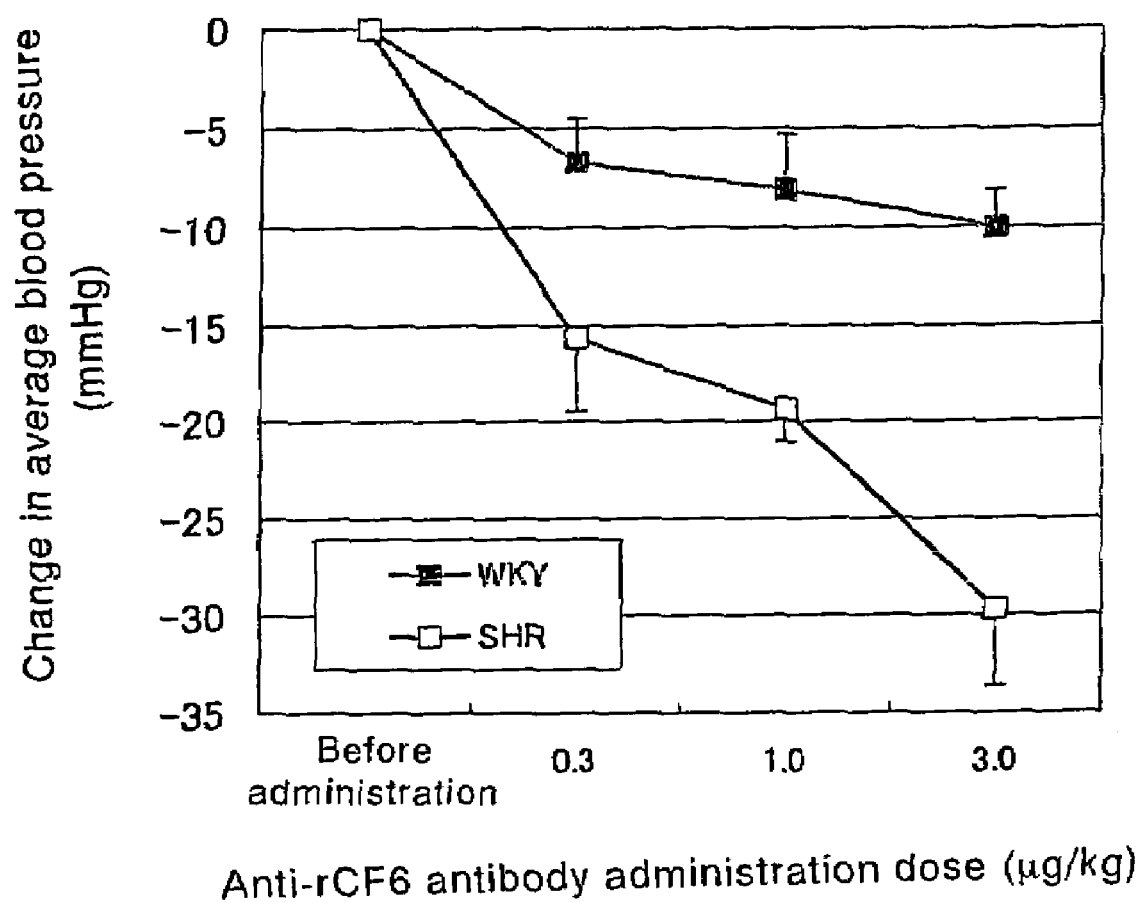
FIG. 8 provides a graph which shows the effects of the anti-rCF6 antibody on rats (SHR and WKY, 16 weeks of age).

SHR and WKY each 16 weeks of age were anesthetized and the anti-rCF6 antibody (0.3, 1.0 and 3.0 µg/kg) was administered by bolus injection into the femoral vein. Then the arterial blood pressure was measured in the open manner from the carotid artery. As a result, the average arterial blood pressure of SHR was lowered in the dose-dependent manner by administering the anti-rCF6 antibody (FIGS. 7 and 8). In WKY, on the other hand, no significant change in the blood pressure was observed due to the administration of the anti-rCF6 antibody (FIG. 8). The administration of a non-specific rabbit antibody (IgG: 10 µg/kg) did not affect the arterial blood pressures of SHR and WKY.

(Effects of the Preadministration of Anti-rCF6 Antibody on Decrease in Rat Blood Pressure due to Bradykinin)

Effects of the anti-rCF6 antibody on the effect of bradykinin of lowering rat blood pressure were examined. SHR and WKY each 16 weeks of age were anesthetized and bradykinin (0.3, 1.0 and 3.0 µg/kg) was cumulatively administered by bolus injection into the femoral vein. Then the arterial blood pressure was measured in the open manner from the carotid artery. Next, the anti-rCF6 antibody (3.0 µg/kg) was administered by bolus injection into the femoral vein and then bradykinin was administered in the same manner. The blood pressure reaction was observed.

Figure 9:
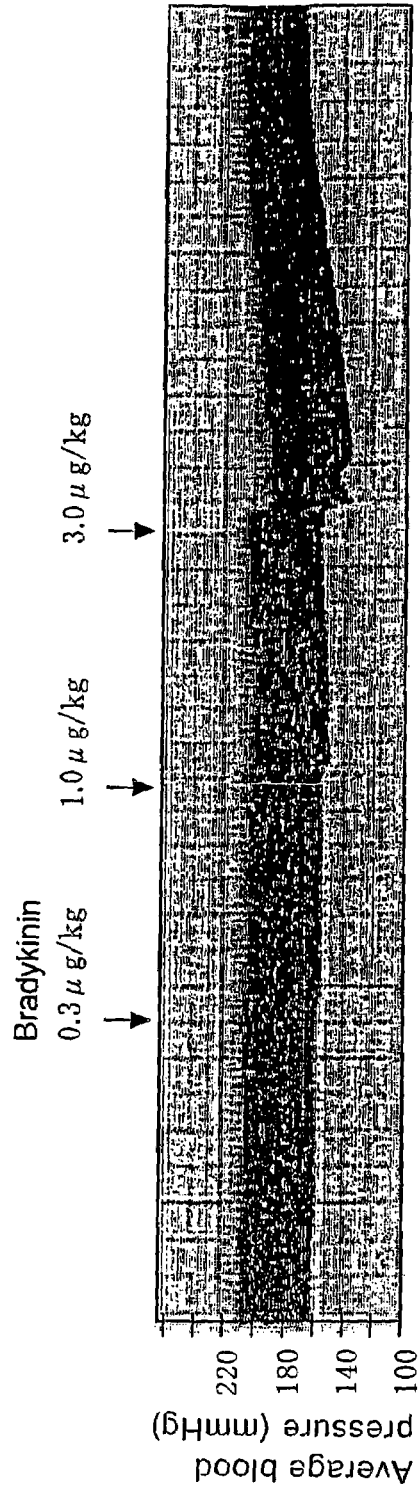
FIG. 9 provides a chart which shows the effects of the preadministration of the anti-rCF6 antibody on the decrease in blood pressure of rats (SHR, 16 weeks of age) caused by bradykinin.
Figure 9:
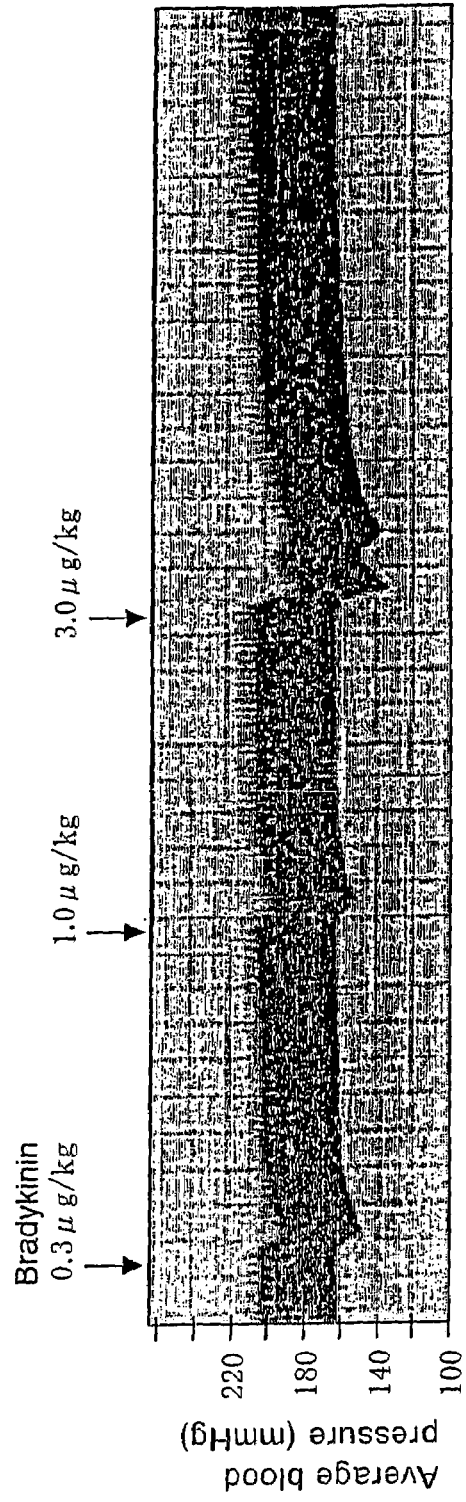
Figure 10:
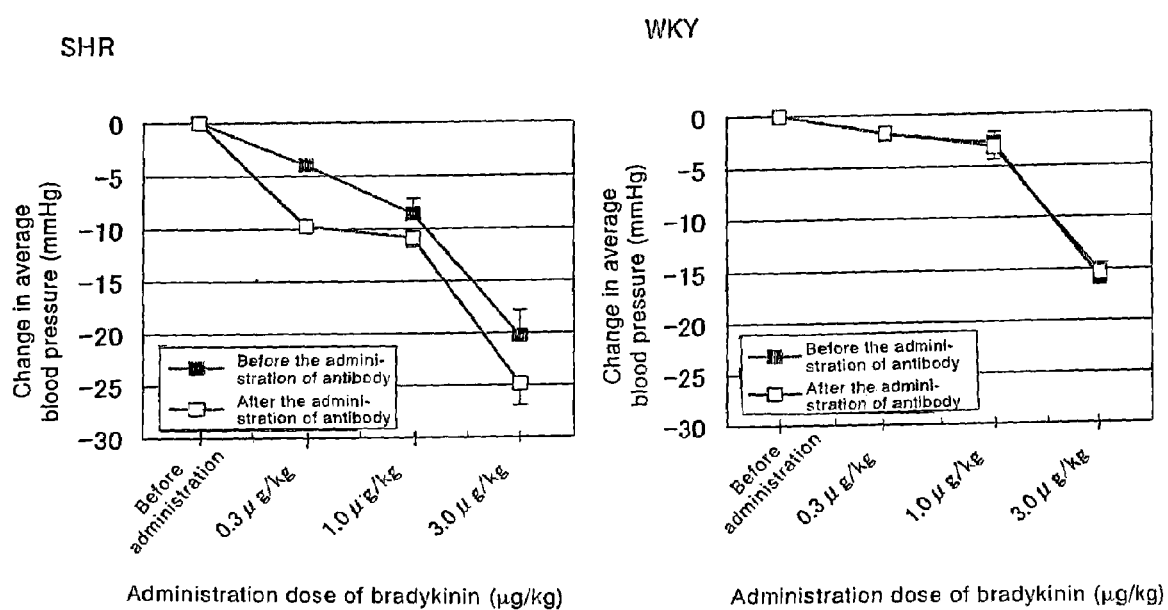
FIG. 10 provides a chart which shows the effects of the preadministration of the anti-rCF6 antibody on the decrease in blood pressure of rats (SHR and WKY, 16 weeks of age) caused by bradykinin.

As a result, the blood pressures of SHR and WKY were dose-dependently lowered by the administration of bradykinin (FIGS. 9-1 and 10). In SHR, the administration of the anti-rCF6 antibody potentiated the effect of bradykinin of lowering blood pressure (FIGS. 9-2 and 10), while no effect was observed in WKY (FIG. 10).

As described above, the anti-rCF6 antibody exerted a hypotensive effect exclusively in the hypertensive state with an increased rCF6 level. Thus, it is indicated that the inhibition of CF6 is efficacious in ameliorating symptoms of diseases caused by the excess of CF6 in the blood.

Example 5

Effects of the Administration of rCF6 on Rat Blood Pressure

Figure 11:
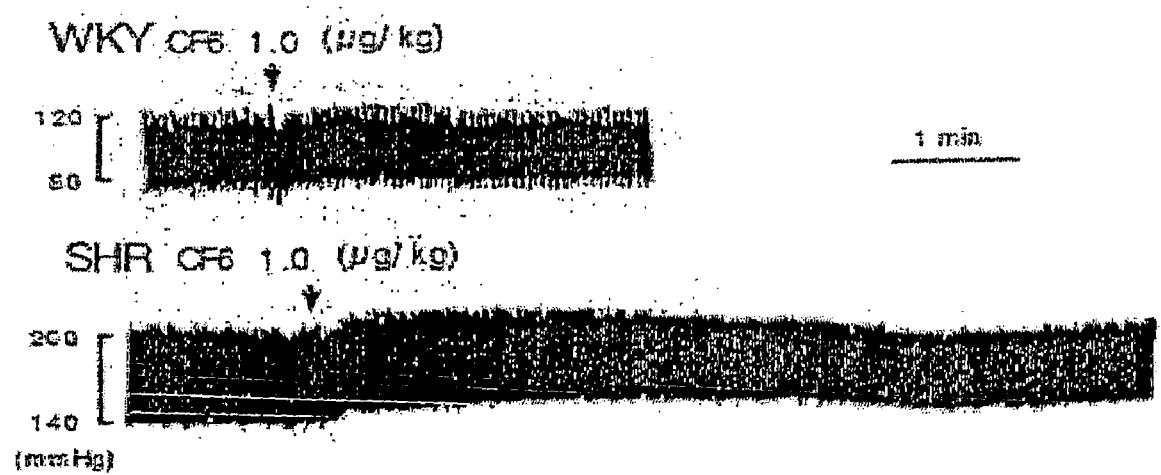
FIG. 11 provides a chart which shows the effects of rCF6 on the blood pressure of rats (SHR and WKY, 16 weeks of age).
Figure 22:
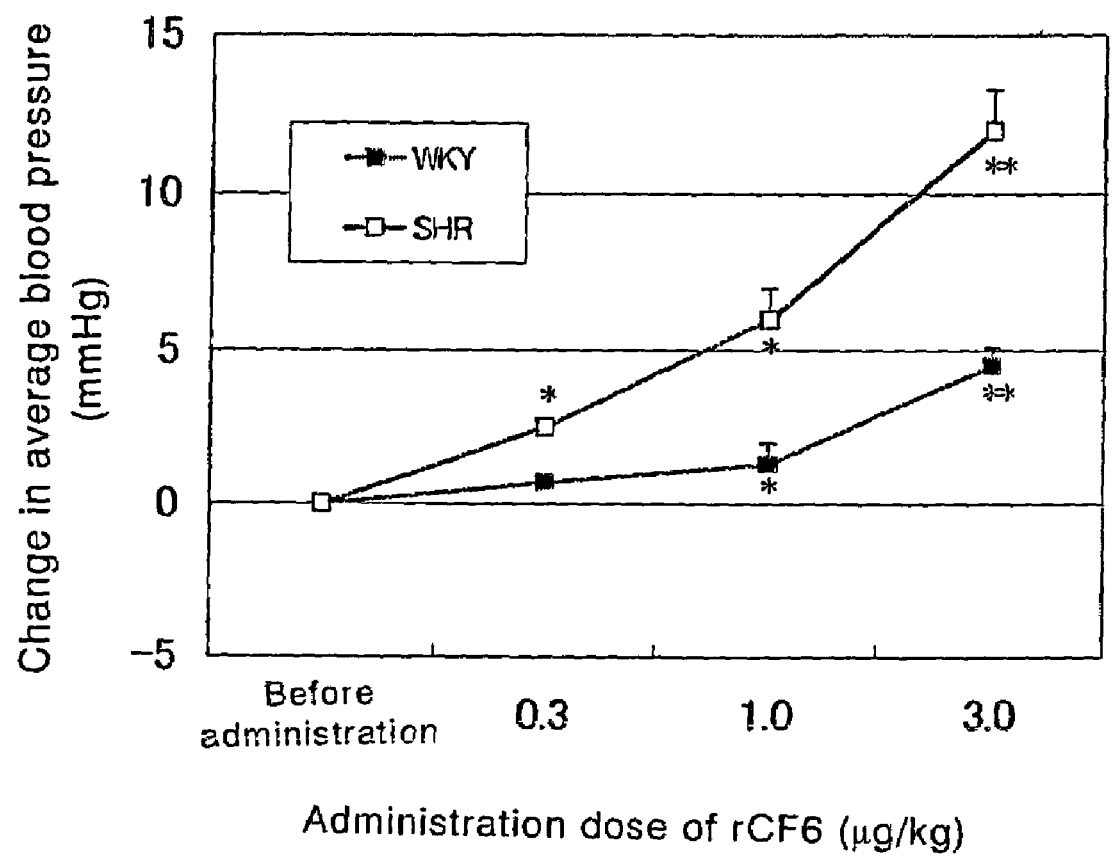
FIG. 22 provides a graph which shows the effects of rCF6 on the blood pressure of rats (SHR and WKY, 16 weeks of age).

Effects of rCF6 on rat blood pressure were examined. SHR or WKY 15 weeks of age were anesthetized and rCF6 (0.3, 1.0 and 3.0 µg/kg) was administered by bolus injection into the femoral vein. Then the arterial blood pressure was measured in an open manner from the carotid artery. As a result, the average arterial blood pressures of SHR and WKY were dose-dependently increased by the administration of rCF6. A remarkable effect was observed in SHR compared with WKY (FIGS. 11 and 22).

Namely, a more remarkable effect of CF6 was observed on SHR having a higher blood CF6 level. This fact indicates that SHR is more sensitive to the effect of CF6.

Considering this result and the hypotensive effect of the anti-rCF6 antibody on SHR observed in Example 4, it is expected that CF6 agonists and CF6 secretion inhibitory drugs would be usable as radical remedies for hypertension which is a disease associated with the excess of CF6 in the blood. Namely, it is indicated that the control of blood CF6 level is efficacious as a method of treating diseases associated with abnormal CF6 level in the blood.

Example 6

Plasma hCF6 Levels of Normal Subjects and Patients with Acute Heart Infarction

Blood samples of 6 normal subjects and 18 patients with acute heart infarction were collected from the vein with the use of a cylinder containing a 1% (w/v) EDTA.2Na solution in ¹/₁₀ dose. All of the patients with acute heart infarction had been successfully treated by percutaneous transluminal coronary angioplasty (PTCA). The blood samples were collected on the day of the onset and the days 2, 3, 5, 7 and 14. Each blood sample thus obtained was centrifuged under cooling to extract the plasma. The plasma was stored at −80° C. until assaying.

A sample for assaying hCF6 was prepared from the plasma in the following manner. Namely, 0.2 ml of 2 N hydrochloric acid was added to 0.8 ml of the plasma and the mixture was allowed to stand at 4° C. for 10 minutes. Next, it was centrifuged at 4° C. at 10,000 rpm for 30 minutes. The supernatant was added to a SepPak C18 column and washed with 5 ml portions of 0.1% (v/v) TFA thrice. After eluting from the column with 2 ml of a 60% (v/v) acetonitrile solution containing 0.1% (v/v) of TFA, the solvent was removed in vacuo and the residue was dissolved in 0.2 to 0.4 ml of RIA buffer to give a sample for RIA.

The hCF6 level was measured as in the case of rCF6 (Example 3) but using recombinant hCF6 as a standard and the anti-hCF6 antibody.

Figure 23:
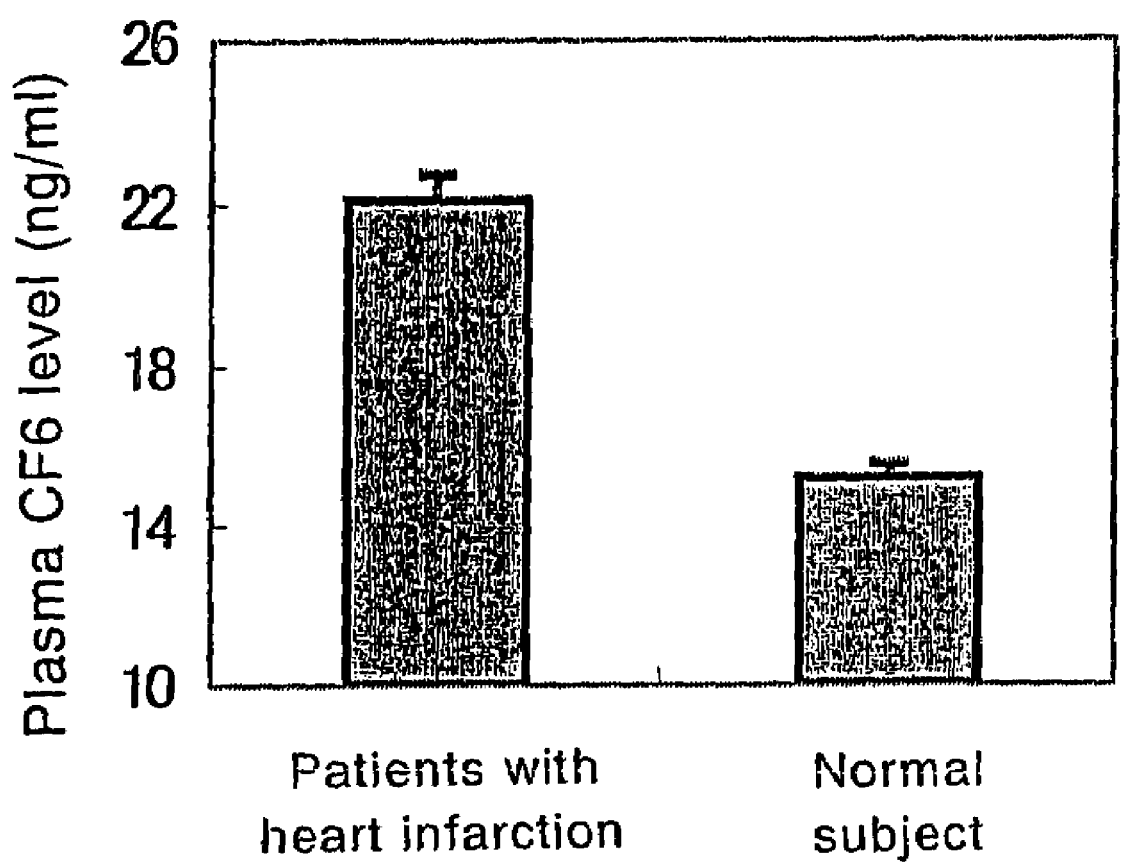
FIG. 23 provides a graph which shows a comparison of the blood hCF6 levels of normal subjects and patients with acute heart infarction.
Figure 24:
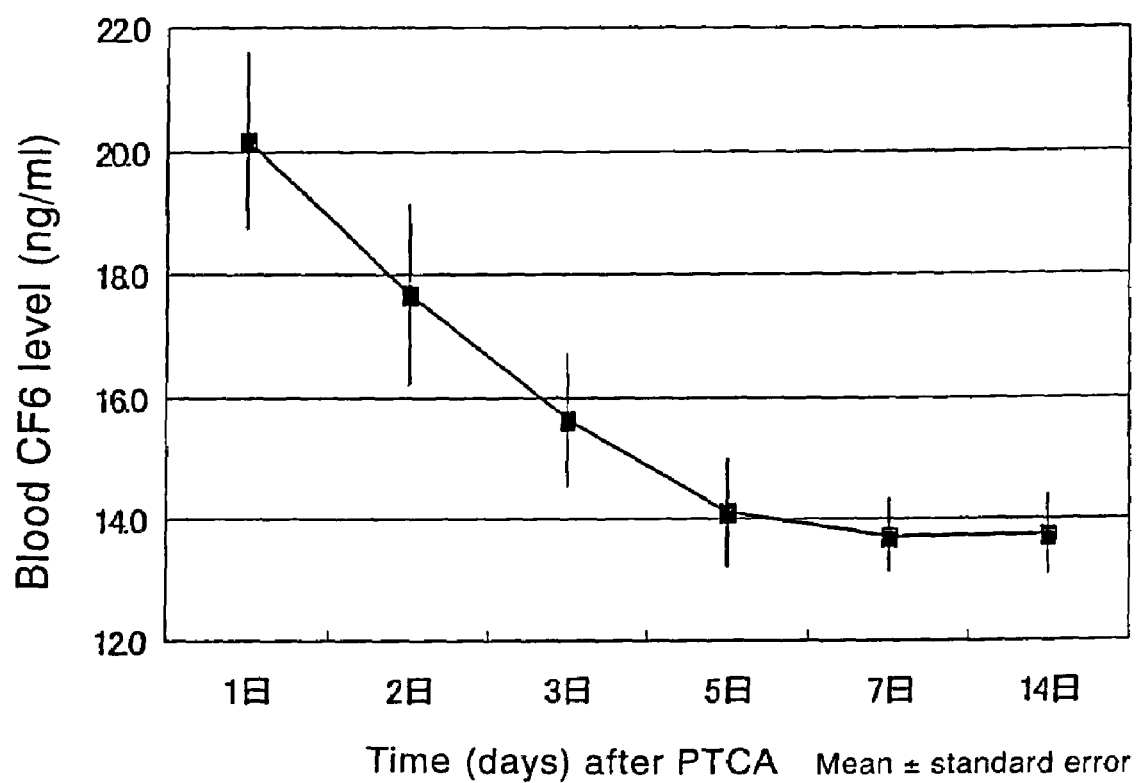
FIG. 24 provides a graph which shows changes in the blood hCF6 level of patients with acute heart infarction.

CF6 was detected at the concentration of 15.2±0.5 ng/ml (mean±standard error) in the normal subject plasma. It is thus confirmed that CF6, which is a protein present in the mitochondrial inner membrane, is present not only in rat blood but also in human blood (FIG. 23). The CF6 level in the plasma of the patients with acute heart infarction showed a peak on the day of the onset or the day 2 and a high plasma CF6 level of 22.1±1.3 ng/ml was observed (FIG. 23). The plasma CF6 levels on the day 1 and day 2 were respectively 20.2±1.4 ng/ml and 17.7±1.5 ng/ml which were significantly higher than the concentration on day 14 (13.7±0.7 ng/ml) (FIG. 24: Fisher's PLSD: p<0.001 and p=0.01). The plasma CF6 levels on the 7 and day 14 were respectively 13.7±0.6 ng/ml and 13.7±0.7 ng/ml, i.e., lowered to the level of the normal subjects.

Thus, it is clarified that the blood CF6 level increases in patients with acute heart infarction. It is therefore suggested that the measurement of the CF6 level might be useful as a diagnostic method for diseases associated with changes in the CF6 level such as acute heart infarction.

Example 7

Release of CF6 Into HUVEC Culture Medium

Figure 25:
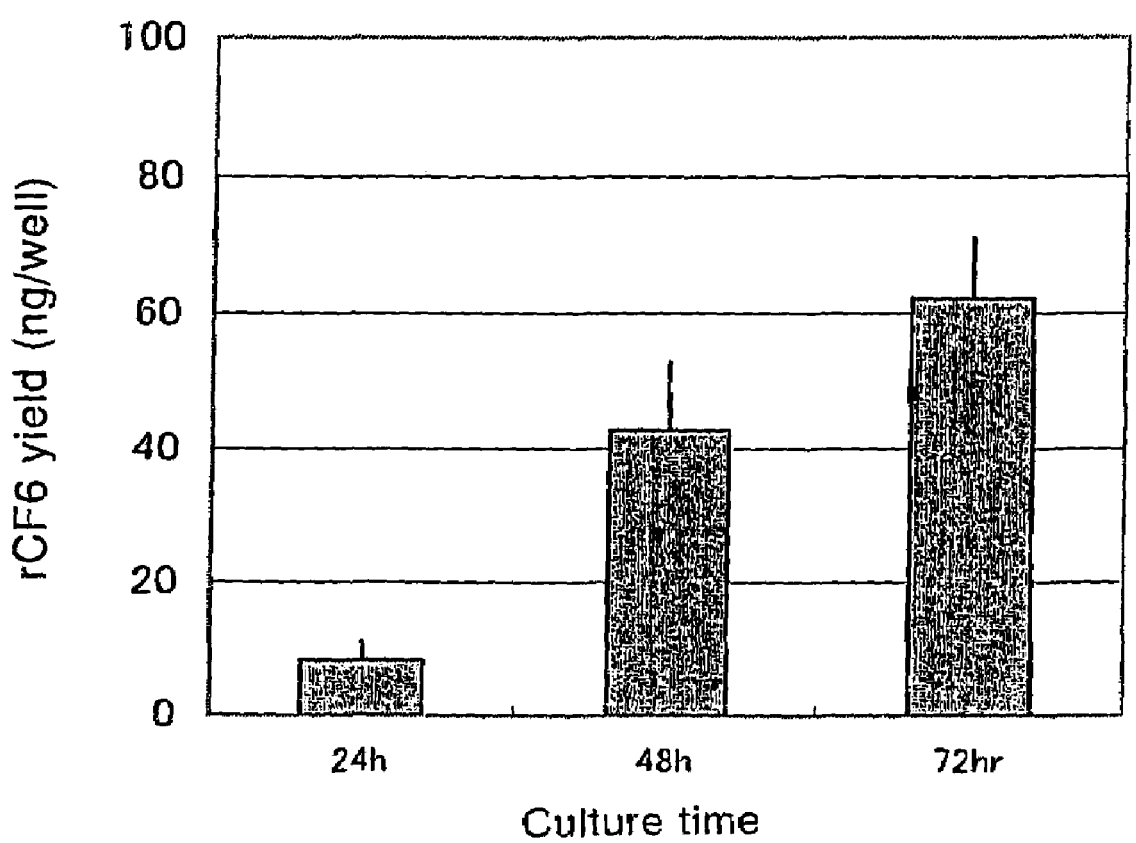
FIG. 25 provides a graph which shows changes in the hCF6 level in a liquid culture of HUVEC.

HUVEC in the confluent state were cultured in a fetal calf serum-free 199 medium in a Petri dish (diameter: 10 cm). After 24, 48 and 72 hours, the culture medium was sampled (n=4 at each point) and hCF6 was quantitated. The culture medium was treated as in Example 6 and the hCF6 level was measured. Thus, it was found out that the CF6 level in the culture medium increased with the passage of time, thus indicating that hCF6 was released from HUVEC (FIG. 25).

Accordingly, CF6 secretion accelerating substances or CF6 secretion inhibitory substances can be obtained by adding candidate compounds to a liquid culture of HUVEC and comparing the amount of CF6 secreted into the culture with a control.

Referential Example 1

Identification of Prostacyclin Production Inhibitor

A prostacyclin production inhibitor was identified as CF6 by the following method.

Figure 12:
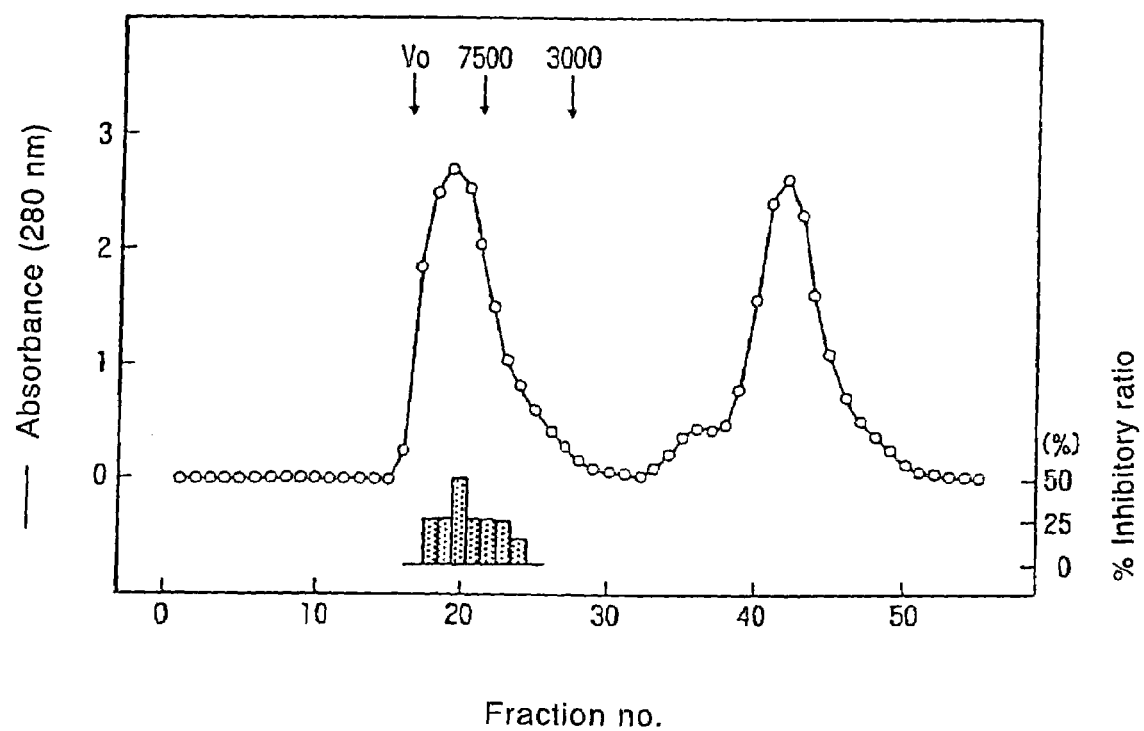
FIG. 12 provides a chart which shows the fractionation with Sephadex G-25 of a boiling water-extract of SHR heart.
Figure 13:
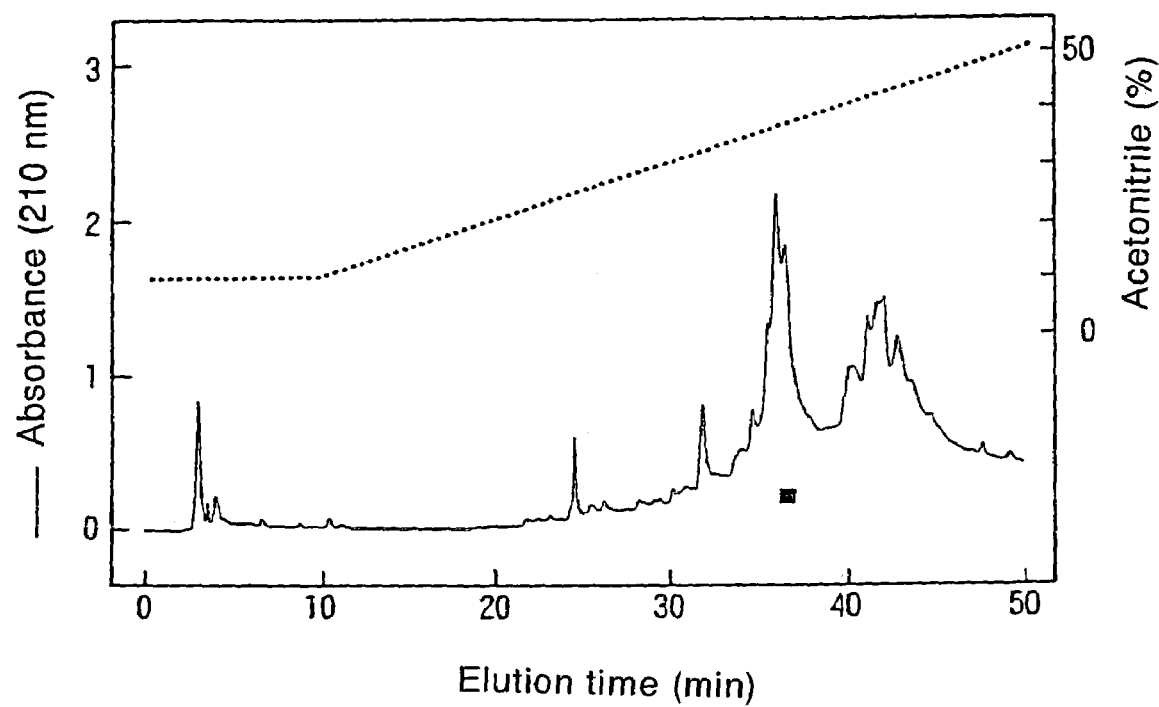
FIG. 13 provides a chart obtained by analyzing the active fraction in the above FIG. 12 by HPLC.

The hearts (152 g) of 187 SHR 16 to 20 weeks of age were allowed to stand in boiling water for 10 minutes. Then peptides were extracted therefrom with 1 N acetic acid. The extract was fractionated in 0.5 ml portions by using Sephadex G-25 (1.5×30 cm) (flow rate: 3 ml/min, FIG. 12). The active fractions (19–21) were separated by HPLC connected to an Inertsil ODS-2 C18 (diameter: 4.6 mm×250 mm) column (GL Science K.K.). After washing with a 20% (v/v) acetonitrile solution containing 0.1% (v/v) of purified TFA for 5 minutes or longer, it was eluted with acetonitrile under a linear gradient (20–60%) for 30 minutes (flow rate: 1 ml/min, FIG. 13). The activity was evaluated by assaying 6-keto-PGFla secreted into the medium obtained from smooth muscle cells originating in SHR mesenteric artery. The purified peptide (FIG. 14) was sequenced as follows. The sequence from the N-terminus to the 39-position was identified by using an amino acid sequence analyzer (PPSQ-10, Shimadzu Corporation) as NKELDPVQKLFLD-KIREYKA KRLASGGPVDTGPEYQQEV (1- to 39-amino acids in SEQ ID NO:2, SEQ ID NO:16). By purifying the fragment digested with AsnN by HPLC connected to YMC-ODS-A302 (diameter: 4.6 mm×150 mm), the subsequent sequences were identified as DRELFKLKQMYGKGEM (40- to 55-amino acids in SEQ ID NO:2, SEQ ID NO:17), DKFPTFNFE (56- to 64-amino acids in SEQ ID NO:2, SEQ ID NO:18), DPKFEVL (65- to 71-amino acids in SEQ ID NO:2, SEQ ID NO:19) and DKPQS (72- to 76-amino acids in SEQ ID NO:2, SEQ ID NO:20). These sequences completely agreed with rCF6 (SEQ ID NO:2) which is a subunit of rat $H^+$ ATP synthase.

Referential Example 2

Preparation of CF6 by Chimeric Protein Expression Method-2

A method of producing rCF6 (SEQ ID NO:2) with the use of factor Xa as a cutting enzyme from a chimeric protein will be illustrated.

(Preparation of rCF6 DNA)

A DNA fragment containing a gene encoding a rCF6 protein having a cofactor Xa recognition sequence Ile Glu Gly Lys (SEQ ID NO:21) added to the N-terminus was obtained by PCR. A rat aorta cDNA library (Clontech) having been treated at 100° C. for 1 minute was used as a template, while CF03 (SEQ ID NO:22) and CF04 (SEQ ID NO:23) were used as primers.

The DNA fragment was cloned into pCRII (pCRIIrCF6Xa) and then the DNA nucleotide sequence was determined to thereby confirm the structure.

SEQ ID NO:22 5'-GATCGAGGGACGTAATAAGG AACTTGATCCT-3'

SEQ ID NO:23 5'-GTCGACTTAGGACTGGGGTT TGTCGA-3'.

(Construction of Expression Vector)

Figure 15:
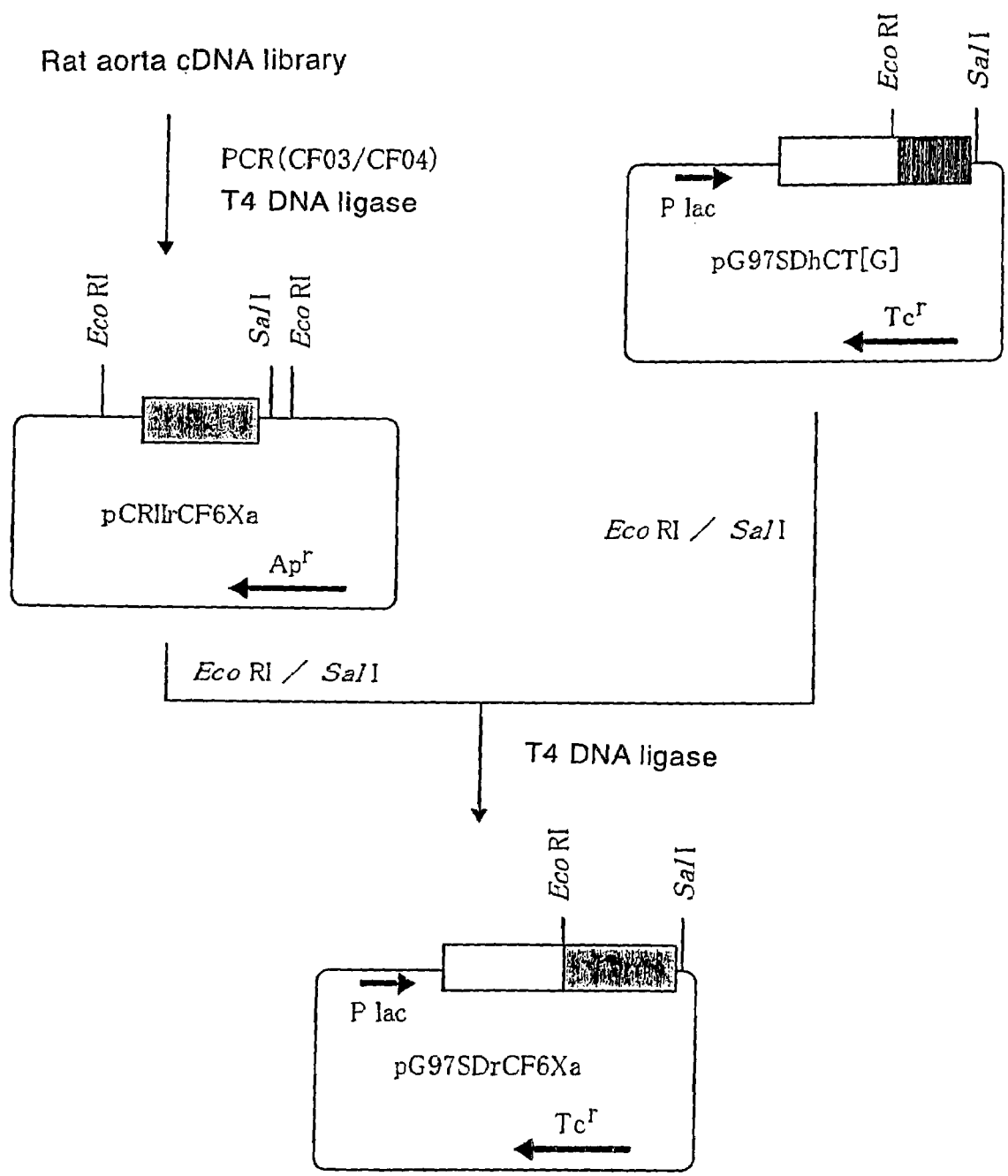
FIG. 15 is a diagram which shows how to construct a vector for expressing a protein containing rCF6 having the recognition sequence of the factor Xa added to the N-terminus from a rat aorta cDNA library.

The plasmid pCRIIrCF6Xa was cut with restriction enzymes EcoRI and SalI to give a 0.3 kb EcoRI-SalI DNA fragment. This DNA fragment had a DNA nucleotide sequence encoding a protein wherein a sequence Glu-Phe-Gly-Leu-Ile-Glu-Gly-Lys (SEQ ID NO:24) having the factor Xa recognition sequence Ile-Glu-Gly-Lys bonded to the C-terminus of a sequence Glu-Phe-Gly-Leu originating in the plasmid pCRII DNA was added to the N-terminus of rCF6 and had the restriction enzyme EcoRI site in the upstream thereof and another restriction enzyme SalI site in the downstream thereof. The plasmid pG97S4DhCT[G] was cut with the restriction enzymes EcoRI and SalI and a DNA fragment of about 3.5 kb containing the vector part was prepared. Then it was ligated to the 0.3 kb EcoRI-SalI DNA fragment to thereby give a plasmid pG97SDrCF6Xa (FIG. 15).

(Expression and Purification of rCF6 Chimeric Protein)

By using the plasmid pG97SDrCF6Xa, E. coli JM109 strain was transformed to give JM109[pG97SDrCF6Xa]. The obtained JM109[pG97SDrCF6Xa] was inoculated into an LB medium containing 10 μg/mL of tetracycline and cultured at 37° C. for 6 hours. Then the liquid culture was inoculated into an SB medium containing 10 μg/mL of tetracycline and 5 mM of MIPTG to give a final turbidity (OD 660 nm) of 0.1 and cultured at 37° C. for 16 hours.

The liquid culture was centrifuged at 6,000 rpm at 4° C. for 10 minutes (20PR-52D, Hitachi, Ltd.) and the cells were collected. The cells were suspended in 20 mM tris hydrochloride (pH 8.0) containing 1 mM of EDTA-Na and disrupted with a French press (10,000 psi; twice).

The disrupted cell suspension was centrifuged at 8,000 rpm at 4° C. (05PR-22, Hitachi Ltd.). The precipitate was suspended in 30 ml of 20 mM tris hydrochloride (pH 8.0) containing 0.5% (w/v) Triton X-100 and centrifuged at 3,000 rpm at 4° C. for 15 minutes. Then, precipitate was collected. This procedure was repeated 4 times to thereby give a partially purified chimeric protein.

(Cutting out of rCF6 From Chimeric Protein and Purification)

To cut out rCF6 from the chimeric protein, 50 μg/mL of the factor Xa (Takara Shuzo Co., Ltd.) was used at a concentration of 3 mg/mL of the chimeric protein and reacted in 50 mM tris hydrochloride (pH 8.0) containing 2 M of urea, 100 mM of NaCl and 1 mM solution of $CaCl_2$ at 37° C. for 4 hours. The liquid reaction mixture was adsorbed by a SepPak C18 column and washed with 0.1% (v/v) of trifluoroacetic acid. Then the peptide was collected in an 80% (v/v) acetonitrile solution containing 0.1% (v/v) of trifluoroacetic acid. The eluate was freeze-dried and then dissolved in 0.1% (v/v) TFA. rCF6 was purified by HPLC connected to YMC-ODS-A302 (% B: 35–50/30 minutes, eluted after 14.5 minutes). The structure of rCF6 was confirmed as in Example 1.

In this method, however, rCF6 was cut off from the chimeric protein only at a low efficiency (about 8%). Therefore, it seems necessary to develop a more efficient method of producing CF6 in order to carry out in vivo experiments, etc. wherein large amounts of CF6 are required.

Referential Example

Inhibition of the Production of Prostacyclin by CF6

Figure 16:
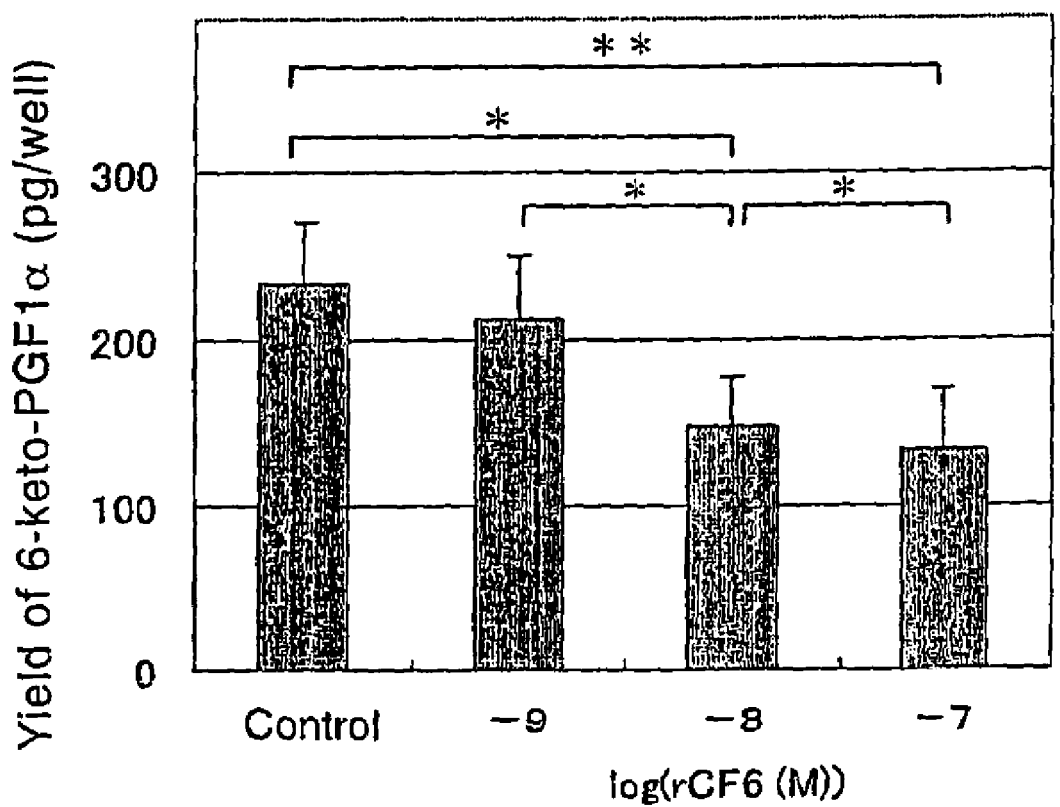
FIG. 16 provides a graph which shows the inhibition of the $PGI_2$ production by rCF6.
Figure 17:
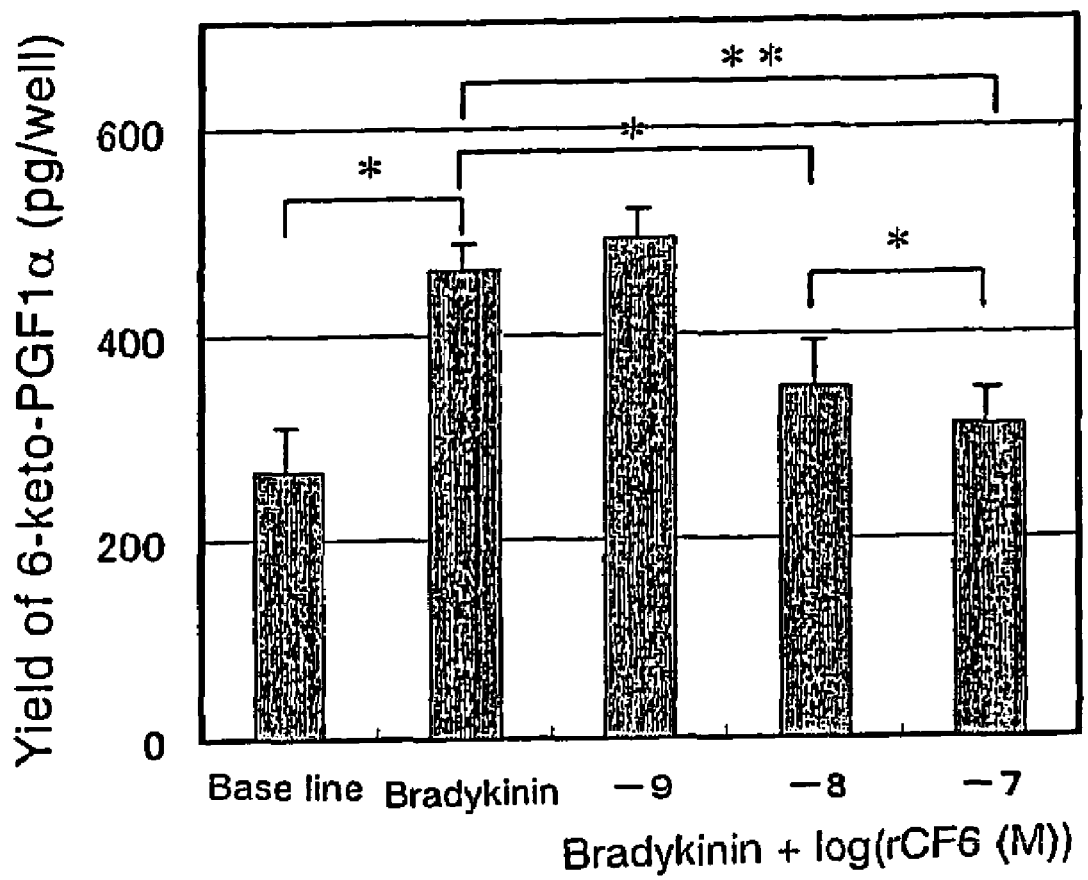
FIG. 17 provides a graph which shows the inhibition of production by rCF6 in the presence of bradykinin.

HUVEC were cultured at 37° C. for 30 minutes in the DMEM containing 1, 10 and 100 nM of rCF6 prepared in Referential Example 2 and thus the inhibition of the $PGI_2$ production by CF6 was examined. The production of $PGI_2$ was measured with the guidance of the amount of 6-keto-PGF1α, which is a stable metabolite of $PGI_2$, secreted into the medium. As a result, CF6 dose-dependently inhibited the $PGI_2$ production (FIG. 16). The same test was carried out in the presence of 1 μM of bradykinin. Thus, it was found out that CF6 dose-independently inhibited the increase in the $PGI_2$ production due to bradykinin (FIG. 17).

Further, 10 nM of CF6 inhibited the increase in the $PGI_2$ production due to 2 μg/ml of ionomycin but not the increase therein due to 10 ng/ml of arachidonic acid and 10 ng/ml of $PGH_2$.

$PGI_2$ is produced starting with a phospholipid. Namely, arachidonic acid cut off from the phospholipid by $PLA_2$ is converted into $PGH_2$ by cyclooxygenase. It is further converted by $PGI_2$ synthase. In this reaction, ionomycin promotes the activation of $PLA_2$, i.e., the cutting off of arachidonic acid from the phospholipid.

Namely, it has been found out that CF6 does not inhibit the production of $PGI_2$ from arachidonic acid or $PGH_2$ which is the downstream product in the arachidonate cascade but inhibits the $PGI_2$ production based on the activation of $PLA_2$. It is thus suggested that the $PGI_2$ production-inhibiting effect of CF6 is based on the inhibition of $PLA_2$.

Referential Example 4

Effect of CF6 of Inhibiting Release of Arachidonic Acid

In Referential Example 3, it is indicated that the $PGI_2$ production-inhibiting effect of CF6 is based on the inhibition of $PLA_2$. On the other hand, $PLA_2$ releasing arachidonic acid from a fatty acid is roughly classified into $Ca^{2+}$-dependent cytoplasmic $PLA_2$ ($cPLA_2$), $Ca^{2+}$-dependent secretory $PLA_2$ ($sPLA_2$) and $Ca^{2+}$-independent $PLA_2$ ($iPLA_2$) depending on the structure and biochemical properties. By using respective inhibitors, it was examined which $PLA_2$ was inhibited by CF6.

Figure 18:
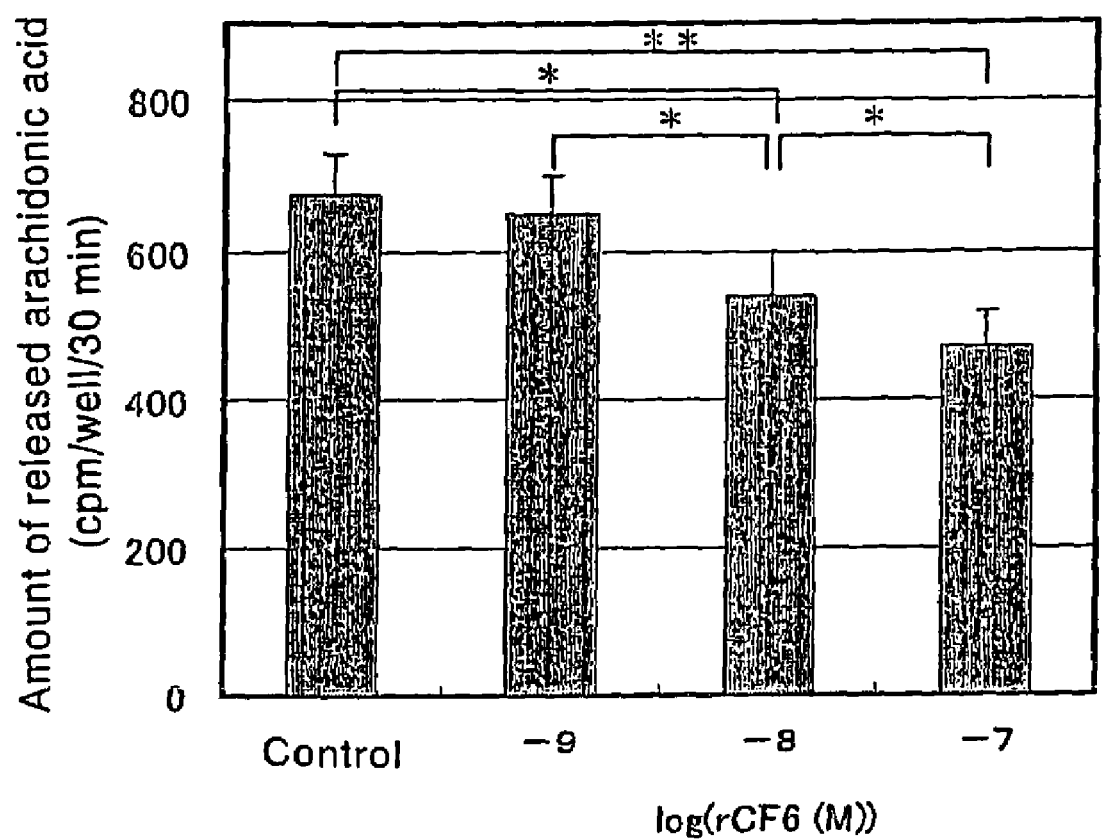
FIG. 18 provides a graph which shows the effect of rCF6 on the release of arachidonic acid from human umbilical venal endothelial cells (HUVEC).
Figure 19:
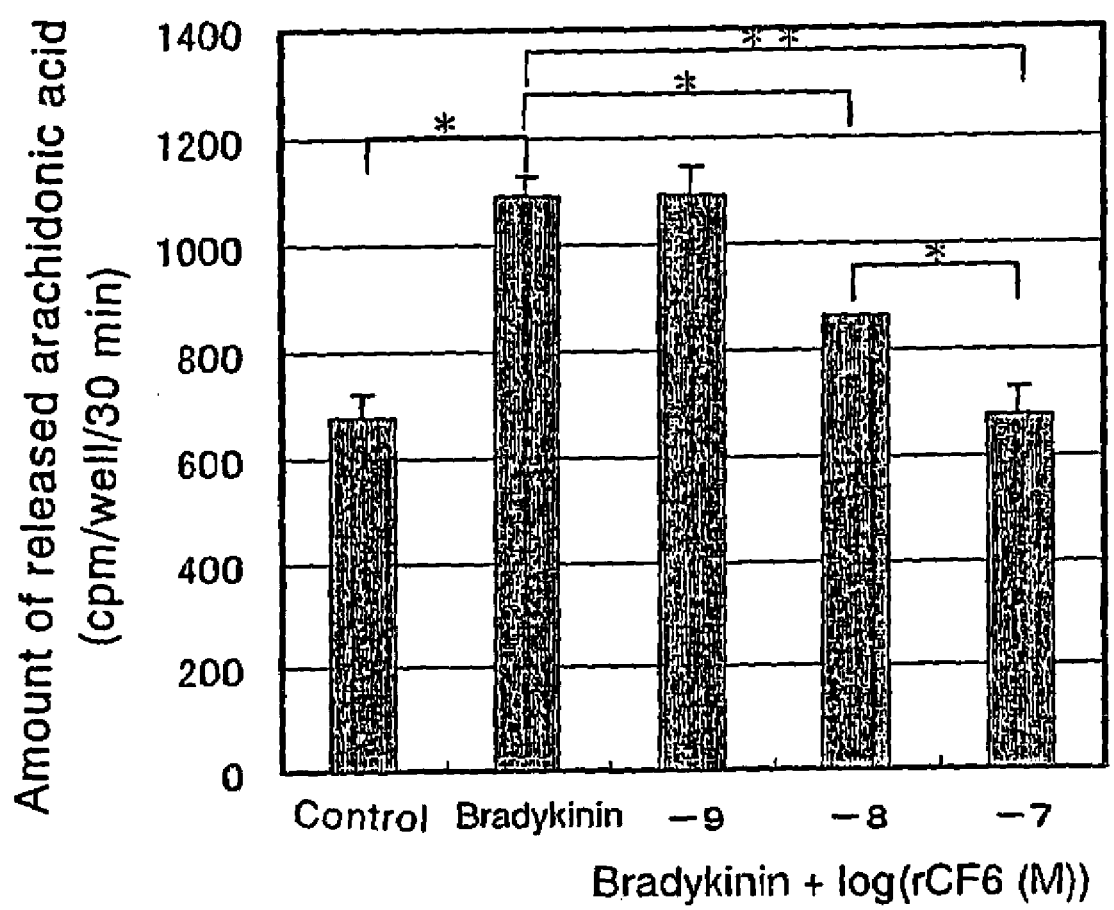
FIG. 19 provides a graph which shows the effect of rCF6 on the effect of bradykinin of releasing arachidonic acid from HUVEC.

HUVEC were cultured for 24 hours in the presence of [$^3$H]-labeled arachidonic acid. Then the medium was replaced by DMEM and the culture was continued in the presence of 1, 10 and 100 mM of CF6 at 37° C. for an additional 30 minutes. Then the release of the [$^3$H]-labeled arachidonic acid into the liquid culture was examined. As a result, CF6 dose-dependently inhibited the release of the [$^3$H]-labeled arachidonic acid (FIG. 18). The same test was carried out in the presence of 1 µM of bradykinin. Thus, it was found out that CF6 dose-dependently inhibited the effect of bradykinin of promoting the release of [$^3$H]-labeled arachidonic acid (FIG. 19).

Figure 20:
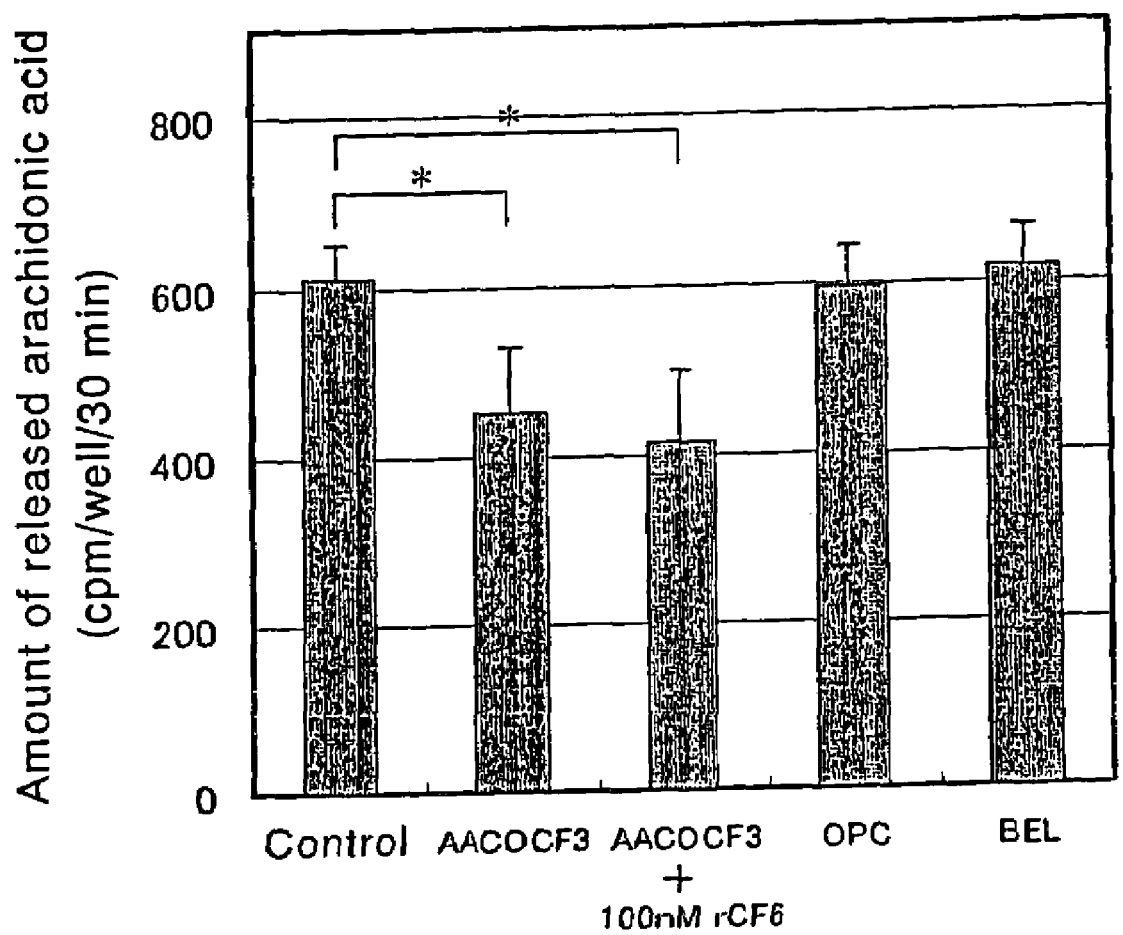
FIG. 20 provides a graph which shows the effects of various $PLA_2$ inhibitors and rCF6 on the release of arachidonic acid from HUVEC.
Figure 21:
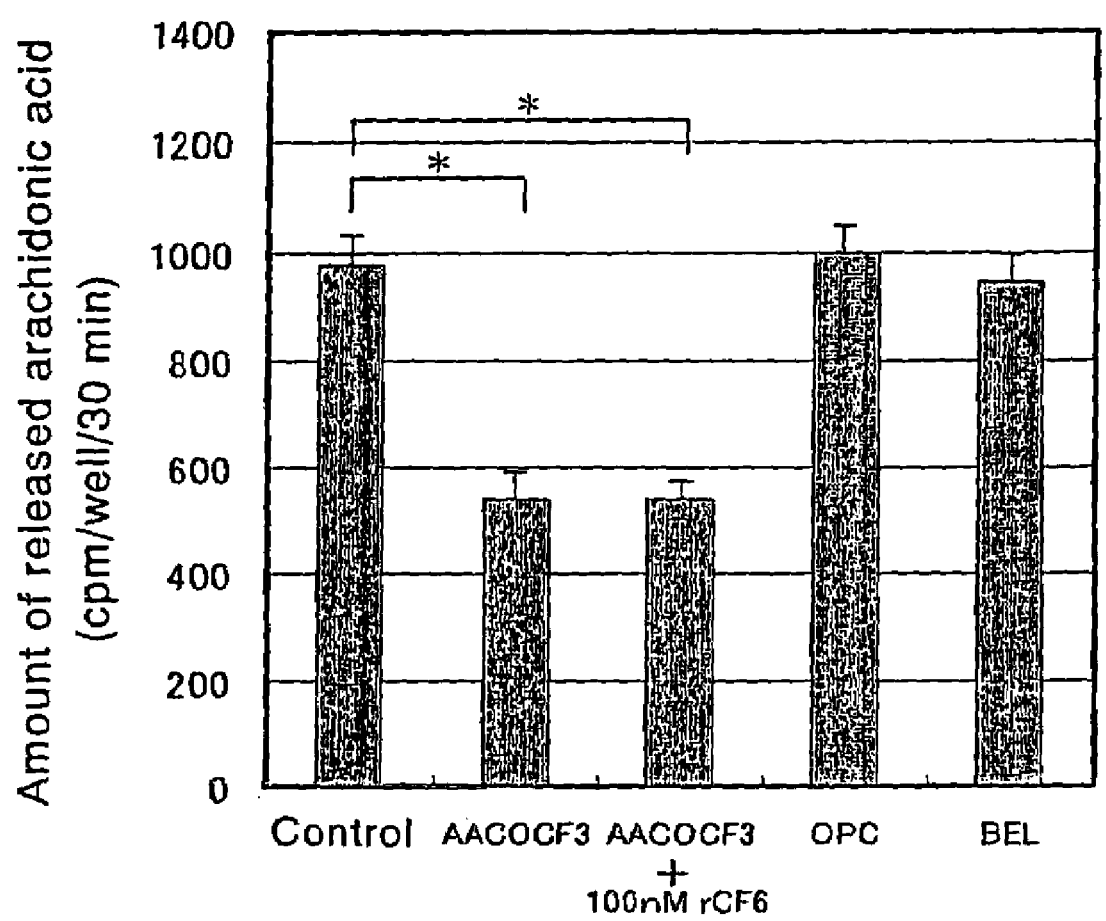
FIG. 21 provides a graph which shows the effects of various $PLA_2$ inhibitors and rCF6 on the effect of bradykinin of releasing arachidonic acid from HUVEC.

Next, the effects of a $cPLA_2$ inhibitor (40 µM of $AACOCF_3$: arachidonic acid 3-fluoromethyl ketone), an $sPLA_2$ inhibitor (1 µM of OPC; oleyloxyethylphosphorylcholine) and an $iPLA_2$ inhibitor (1 µM of BEL: bromoenolcholine) of inhibiting the release of arachidonic acid form HUVEC were examined. As a result, it was found out that, in HUVEC, the $cPLA_2$ inhibitor alone inhibited the release of arachidonic acid. Namely, the $PLA_2$ participating in the release of arachidonic acid is $cPLA_2$ (FIGS. 20 and 21).

$cPLA_2$ shows a high specificity to arachidonic acid-containing phospholipids and selectively releases arachidonic acid at a $Ca^{2+}$ concentration of µM order. As the results of experiments with the use of mice with the hyperexpression of c $PLA_2$ and mice lacking $cPLA_2$, it has been clarified that $cPLA_2$ plays an important role not only in the metabolism of arachidonic acid in the immediate phase but in the delayed phase of arachidonic acid which is important in inflammatory reactions. Therefore, it is expected that the inhibition of $cPLA_2$ induces a strong inflammatory reaction (Uozumi N., et al. 390 618–622, 1997).

INDUSTRIAL APPLICABILITY

The present invention provides an antibody specific to CF6 and diagnostic methods for pathological conditions in which CF6 participates. The present invention also provides a method of treating diseases such as hypertension on the basis of the inhibition of CF6 in the blood whereby normal blood pressure is not lowered. Moreover, the diagnostic methods according to the present invention contribute to the provision of methods of treating pathological conditions associated with an increase or decrease in CF6 in the blood.

What is claimed is:

1. A method of diagnosing a disease associated with an increase in the CF6 level in the blood, which comprises the CF6 level in a collected blood sample being measured by use of a diagnostic aid comprising an anti-CF6 antibody, and said disease is diagnosed when said CF6 blood level increases as compared to normal subjects' CF6 blood level.

2. The diagnostic method according to claim 1 wherein said disease with an increase in the CF6 level in the blood is acute heart infarction.

3. A method according to claim 1 wherein said anti-CF6 antibody is prepared by using the whole human CF6 (SEQ ID NO:1) or rat CF6 (SEQ ID NO:2) or a part thereof as an antigen.

4. A method according to claim 1 wherein said disease associated with an increase in the CF6 level in the blood is heart infarction, angina pectoris, heart failure, pulmonary hypertension, hypertension, cerebrovascular disorder, arteriosclerosis obliterans, arteriosclerosis, hyperlipemia, diabetes, bronchial disease, stomach ulcer, eclampsia of pregnancy, hemolytic-uremic syndrome or thrombocytopenic purpura.

5. A method according to claim 1, wherein the collected blood samples are collected prior to disease onset and during the disease.

6. A method of diagnosing a disease associated with an increase in the CF6 level in the blood, which comprises the CF6 level in a collected blood sample being measured by use of an anti-CF6 antibody, and said disease is diagnosed when said CF6 blood level increases as compared to normal subjects' CF6 blood level.

7. A method according to claim 6 wherein said anti-CF6 antibody is prepared by using the whole human CF6 (SEQ ID NO:1) or rat CF6 (SEQ ID NO:2) or a part thereof as an antigen.

8. A method according to claim 6 wherein said disease associated with an increase in the CF6 level in the blood is heart infarction, angina pectoris, heart failure, pulmonary hypertension, hypertension, cerebrovascular disorder, arteriosclerosis obliterans, arteriosclerosis, hyperlipemia, diabetes, bronchial disease, stomach ulcer, eclampsia of pregnancy, hemolytic-uremic syndrome or thrombocytopenic purpura.

9. A method according to claim 6, wherein the collected blood samples are collected prior to disease onset and during the disease.

10. A method of measuring the CF6 level in blood by use of an anti-CF6 antibody or a diagnostic aid comprising an anti-CF6 antibody.

11. A method according to claim 10 wherein said anti-CF6 antibody is prepared by using the whole human CF6 (SEQ ID NO:1) or rat CF6 (SEQ ID NO:2) or a part thereof as an antigen.

* * * * *

SEQUENCE LISTING

```
<160> NUMBER OF SEQ ID NOS: 24

<210> SEQ ID NO 1
<211> LENGTH: 76
<212> TYPE: PRT
<213> ORGANISM: Human

<400> SEQUENCE: 1

Asn Lys Glu Leu Asp Pro Ile Gln Lys Leu
 1               5                  10

Phe Val Asp Lys Ile Arg Glu Tyr Lys Ser
                15                  20

Lys Arg Gln Thr Ser Gly Gly Pro Val Asp
                25                  30

Ala Ser Ser Glu Tyr Gln Gln Glu Leu Glu
                35                  40

Arg Glu Leu Phe Lys Leu Lys Gln Met Phe
                45                  50

Gly Asn Ala Asp Met Asn Thr Phe Pro Thr
                55                  60

Phe Lys Phe Glu Asp Pro Lys Phe Glu Val
                65                  70

Leu Glu Lys Pro Gln Ala
                75

<210> SEQ ID NO 2
<211> LENGTH: 76
<212> TYPE: PRT
<213> ORGANISM: Rat
```

-continued

```
<400> SEQUENCE: 2

Asn Lys Glu Leu Asp Pro Val Gln Lys Leu
 1               5                  10

Phe Leu Asp Lys Ile Arg Glu Tyr Lys Ala
                15                  20

Lys Arg Leu Ala Ser Gly Gly Pro Val Asp
                25                  30

Thr Gly Pro Glu Tyr Gln Gln Glu Val Asp
                35                  40

Arg Glu Leu Phe Lys Leu Lys Gln Met Tyr
                45                  50

Gly Lys Gly Glu Met Asp Lys Phe Pro Thr
                55                  60

Phe Asn Phe Glu Asp Pro Lys Phe Glu Val
                65                  70

Leu Asp Lys Pro Gln Ser
                75

<210> SEQ ID NO 3
<211> LENGTH: 5
<212> TYPE: PRT
<213> ORGANISM: Unknown
<220> FEATURE:
<221> NAME/KEY:
<222> LOCATION:
<223> OTHER INFORMATION: Enterokinase recognition site

<400> SEQUENCE: 3

Asp Asp Asp Asp Lys
 1               5

<210> SEQ ID NO 4
<211> LENGTH: 139
<212> TYPE: PRT
<213> ORGANISM: E. coli

<400> SEQUENCE: 4

Thr Met Ile Thr Asp Ser Leu Ala Val Val Leu Gln Arg Arg Asp
 1               5                  10                  15

Trp Glu Asn Pro Gly Val Thr Gln Leu Asn Arg Leu Ala Ala His
                20                  25                  30

Pro Pro Phe Ala Ser Trp Arg Asn Ser Glu Glu Ala Arg Thr Asp
                35                  40                  45

Arg Pro Ser Gln Gln Leu Arg Ser Leu Asn Gly Glu Trp Arg Phe
                50                  55                  60

Ala Trp Phe Pro Ala Pro Glu Ala Val Pro Glu Ser Leu Leu Glu
                65                  70                  75

Ser Asp Leu Pro Glu Ala Asp Thr Val Val Pro Ser Asn Trp
                80                  85                  90

Gln Met His Gly Tyr Asp Ala Pro Ile Tyr Thr Asn Val Thr Tyr
                95                  100                 105

Pro Ile Thr Val Asn Pro Pro Phe Val Pro Thr Glu Asn Pro Thr
                110                 115                 120

Gly Ser Tyr Ser Leu Thr Phe Asn Val Asp Glu Ser Trp Leu Gln
                125                 130                 135

Glu Gly Gln Thr
```

<210> SEQ ID NO 5
<211> LENGTH: 97
<212> TYPE: PRT
<213> ORGANISM: E. coli

<400> SEQUENCE: 5

Thr Met Ile Thr Asp Ser Leu Ala Val Val Leu Gln Arg Arg Asp
 1               5                  10                  15

Trp Glu Asn Pro Gly Val Thr Gln Leu Asn Arg Leu Ala Ala His
                20                  25                  30

Pro Pro Phe Ala Ser Trp Arg Asn Ser Asp Asp Ala Arg Thr Asp
                35                  40                  45

Arg Pro Ser Gln Gln Leu Arg Ser Leu Asn Gly Glu Trp Arg Phe
                50                  55                  60

Ala Trp Phe Pro Ala Pro Glu Ala Val Pro Asp Ser Leu Leu Asp
                65                  70                  75

Ser Asp Leu Pro Glu Ala Asp Thr Val Val Val Pro Ser Asn Trp
                80                  85                  90

Gln Met His Gly Tyr Asp Ala
                95

<210> SEQ ID NO 6
<211> LENGTH: 23
<212> TYPE: DNA
<213> ORGANISM: Artificial Sequence
<220> FEATURE:
<221> NAME/KEY:
<222> LOCATION:
<223> OTHER INFORMATION: Primer used in PCR method

<400> SEQUENCE: 6
atgactgttc agaggatctt cag                                           23

<210> SEQ ID NO 7
<211> LENGTH: 27
<212> TYPE: DNA
<213> ORGANISM: Artificial Sequence
<220> FEATURE:
<221> NAME/KEY:
<222> LOCATION:
<223> OTHER INFORMATION: Primer used in PCR method

<400> SEQUENCE: 7
gtcgactcag gactggggtt tgtcgag                                       27

<210> SEQ ID NO 8
<211> LENGTH: 23
<212> TYPE: DNA
<213> ORGANISM: Artificial Sequence
<220> FEATURE:
<221> NAME/KEY:
<222> LOCATION:
<223> OTHER INFORMATION: Primer used in PCR method

<400> SEQUENCE: 8
atgattcttc agaggctctt cag                                           23

<210> SEQ ID NO 9
<211> LENGTH: 28
<212> TYPE: DNA
<213> ORGANISM: Artificial Sequence
<220> FEATURE:
<221> NAME/KEY:
<222> LOCATION:
<223> OTHER INFORMATION: Primer used in PCR method

```
<400> SEQUENCE: 9
gtcgactcag gcctggggtt tttcgatg                                    28

<210> SEQ ID NO 10
<211> LENGTH: 45
<212> TYPE: DNA
<213> ORGANISM: Artificial Sequence
<220> FEATURE:
<221> NAME/KEY:
<222> LOCATION:
<223> OTHER INFORMATION: Gene coding for enterokinase recognition site
      and Eco RI recognition site

<400> SEQUENCE: 10
gaattcgacg atgacgataa gaataaggaa cttgatcctg tacag                45

<210> SEQ ID NO 11
<211> LENGTH: 46
<212> TYPE: DNA
<213> ORGANISM: Artificial Sequence
<220> FEATURE:
<221> NAME/KEY:
<222> LOCATION:
<223> OTHER INFORMATION: Gene coding for enterokinase recognition site
      and Eco RI recognition site

<400> SEQUENCE: 11
gaattcgacg atgacgataa gaataaggaa cttgatccta tacaga              46

<210> SEQ ID NO 12
<211> LENGTH: 20
<212> TYPE: PRT
<213> ORGANISM: rat

<400> SEQUENCE: 12

Cys Phe Pro Thr Phe Asn Phe Glu Asp Pro Lys Phe Glu Val Leu
  1               5                  10                  15

Asp Lys Pro Gln Ser
             20

<210> SEQ ID NO 13
<211> LENGTH: 20
<212> TYPE: PRT
<213> ORGANISM: rat

<400> SEQUENCE: 13

Tyr Phe Pro Thr Phe Asn Phe Glu Asp Pro Lys Phe Glu Val Leu
  1               5                  10                  15

Asp Lys Pro Gln Ser
             20

<210> SEQ ID NO 14
<211> LENGTH: 19
<212> TYPE: PRT
<213> ORGANISM: human

<400> SEQUENCE: 14

Cys Leu Phe Val Asp Lys Ile Arg Glu Tyr Lys Ser Lys Arg Gln
  1               5                  10                  15

Thr Ser Gly Gly
```

<210> SEQ ID NO 15
<211> LENGTH: 18
<212> TYPE: PRT
<213> ORGANISM: human

<400> SEQUENCE: 15

Leu Phe Val Asp Lys Ile Arg Glu Tyr Lys Ser Lys Arg Gln Thr
 1               5                  10                  15
Ser Gly Gly

<210> SEQ ID NO 16
<211> LENGTH: 39
<212> TYPE: PRT
<213> ORGANISM: rat

<400> SEQUENCE: 16

Asn Lys Glu Leu Asp Pro Val Gln Lys Leu Phe Leu Asp Lys Ile
 1               5                  10                  15
Arg Glu Tyr Lys Ala Lys Arg Leu Ala Ser Gly Gly Pro Val Asp
                20                  25                  30
Thr Gly Pro Glu Tyr Gln Gln Glu Val
                35

<210> SEQ ID NO 17
<211> LENGTH: 16
<212> TYPE: PRT
<213> ORGANISM: rat

<400> SEQUENCE: 17

Asp Arg Glu Leu Phe Lys Leu Lys Gln Met Tyr Gly Lys Gly Glu
 1               5                  10                  15
Met

<210> SEQ ID NO 18
<211> LENGTH: 9
<212> TYPE: PRT
<213> ORGANISM: rat

<400> SEQUENCE: 18

Asp Lys Phe Pro Thr Phe Asn Phe Glu
 1               5

<210> SEQ ID NO 19
<211> LENGTH: 7
<212> TYPE: PRT
<213> ORGANISM: rat

<400> SEQUENCE: 19

Asp Pro Lys Phe Glu Val Leu
 1               5

<210> SEQ ID NO 20
<211> LENGTH: 5
<212> TYPE: PRT
<213> ORGANISM: rat

<400> SEQUENCE: 20

Asp Lys Pro Gln Ser
 1               5

```
<210> SEQ ID NO 21
<211> LENGTH: 4
<212> TYPE: PRT
<213> ORGANISM: Artificial Sequence
<220> FEATURE:
<221> NAME/KEY:
<222> LOCATION:
<223> OTHER INFORMATION: Factor Xa recognition site

<400> SEQUENCE: 21

Ile Glu Gly Lys

<210> SEQ ID NO 22
<211> LENGTH: 31
<212> TYPE: DNA
<213> ORGANISM: Artificial Sequence
<220> FEATURE:
<221> NAME/KEY:
<222> LOCATION:
<223> OTHER INFORMATION: Primer for PCR method

<400> SEQUENCE: 22
gatcgaggga cgtaataagg aacttgatcc t                            31

<210> SEQ ID NO 23
<211> LENGTH: 26
<212> TYPE: DNA
<213> ORGANISM: Artificial Sequence
<220> FEATURE:
<221> NAME/KEY:
<222> LOCATION:
<223> OTHER INFORMATION: Primer for PCR method

<400> SEQUENCE: 23
gtcgacttag gactggggtt tgtcga                                  26

<210> SEQ ID NO 24
<211> LENGTH: 8
<212> TYPE: PRT
<213> ORGANISM: Artificial Sequence
<220> FEATURE:
<221> NAME/KEY:
<222> LOCATION:
<223> OTHER INFORMATION: Factor Xa recognition site containig peptide

<400> SEQUENCE: 24

Glu Phe Gly Leu Ile Glu Gly Lys
 1               5
```